US006770633B1

(12) United States Patent
Robbins et al.

(10) Patent No.: US 6,770,633 B1
(45) Date of Patent: Aug. 3, 2004

(54) RIBOZYME THERAPY FOR THE TREATMENT OF PROLIFERATIVE SKIN AND EYE DISEASES

(75) Inventors: Joan M. Robbins, San Diego, CA (US); Richard Tritz, San Diego, CA (US)

(73) Assignee: Immusol, Inc., San Diego, CA (US)

( * ) Notice: Subject to any disclaimer, the term of this patent is extended or adjusted under 35 U.S.C. 154(b) by 0 days.

(21) Appl. No.: 09/696,791

(22) Filed: Oct. 25, 2000

Related U.S. Application Data
(60) Provisional application No. 60/161,532, filed on Oct. 26, 1999.

(51) Int. Cl.[7] .................. C07H 21/04; A61K 48/00; C12Q 1/68; C12P 19/34
(52) U.S. Cl. ..................... 514/44; 435/6; 435/91.3; 536/24.5; 536/23.2
(58) Field of Search ................ 435/6, 91.1, 91.3, 435/325, 375; 536/24.5; 514/44

(56) References Cited

U.S. PATENT DOCUMENTS

| | | | |
|---|---|---|---|
| 5,646,042 A | 7/1997 | Stinchcomb et al. | |
| 5,658,780 A | 8/1997 | Stinchcomb et al. | |
| 5,929,040 A | 7/1999 | Werther et al. | |
| 6,103,890 A | 8/2000 | Jarvis et al. | |
| 6,132,967 A | 10/2000 | Grimm et al. | |

FOREIGN PATENT DOCUMENTS

WO   WO 00/32765   6/2000

OTHER PUBLICATIONS

Green et al. Antisense oligonucleotides: An Evolving Technology for the Modulation of Gene Expression in Human Disease. J. Am. Coll. Surg. vol. 191, No. 1, Jul. 2000.*

Branch. A.D. A good antisense molecule is hard to find. TIBS 23. Feb. 1998, pp. 45–50.*

Agrawal et al. Antisense therapeutics: is it as simple as complementary base recognition? Molecular Medicine Today. Feb. 2000, vol. 6, pp. 72–81.*

Jen et al. Supression of Gene Expression by Targeted Disruption of Messenger RNA: Available Options and Current Strategies. Stem Cells 2000: 18: 307–319.*

Verma et al. Gene therapy– promises, problems and prospects. Nature. Vol. 389, Sep. 18, 1997, pp. 239–242.*

Anderson, W. F Human Gene Therapy. Nature. Vol. 392. Apr. 30, 1998. Pp. 25–30.*

Dsau. V. Transcription Factor Decoy. Circulation Research. Vol. 90. Pp. 1234–1236. 2002.*

Frimerman et al., "Chimeric DNA–RNA Hammerhead Ribozyme to Proliferating Cell Nuclear Antigen Reduces Stent–Induced Stenosis in a Porcine Coronary Model." *Circulation* 99:697–703, Feb. 9, 1999.

LaVail et al., "Ribozyme rescue of photoreceptor cells in P23H transgenic rats: Long–term survival and late–stage therapy." *Proceedings National Academy Science USA* 97(21):11488–11493, Oct. 10, 2000.

Flores–Aguilar et al., "Evaluation of Retinal Toxicity and Efficacy of Anti–Cytomegalovirus and Anti–Herpes Simplex Virus Antiviral Phosphorothioate Oligonucleotides ISIS 2922 and ISIS 4015," *The Journal of Infectious Diseases* 175: 1308–1316, Jun. 1997.

(List continued on next page.)

Primary Examiner—Karen A. Lacourciere
(74) Attorney, Agent, or Firm—Law Office of David Spolter

(57) ABSTRACT

As an effective therapy for proliferative skin and eye diseases such as psoriasis and proliferative diabetic retinopathy, this invention provides ribozymes and ribozyme delivery systems which cleave RNA encoding cytokines involved in inflammation, matrix metalloproteinases, a cyclin, a cell-cycle dependent kinase, a growth factor, or a reductase.

28 Claims, 13 Drawing Sheets

OTHER PUBLICATIONS

Taylor et al., "Chimeric DNA–RNA hammerhead ribozymes have enhanced in vitro catalytic efficiency and increased stability in vivo." *Nucleic Acids Research* 20(17):4559–4565, 1992.

Morita et al., "Inhibition Of Rheumatoid Synovial Fibroblast Proliferation By Antisense Oligonucleotides Targeting Proliferating Cell Nuclear Antigen Messenger RNA," *Arthritis Rheumatism* 40(7): 1292–1297, Jul. 1997.

Gillardon et al., "Inhibition of e–Fos expression in the UV–irradiated epidermis by topical application of antisense oligodeoxynucleotides suppresses activation of proliferating cell nuclear antigen," *Carcinogenesis* 16(8): 1853–1856, 1995.

Jaskulski et al., "Inhibition of Cellular Proliferation by Antisense Oligodeoxynucleotides to PCNA Cyclin," *Science* 240: 1544–1546, Jun. 10, 1988.

Capeans et al., "A c–myc Antisense Oligonucleotide Inhibits Human Retinal Pigment Epithelial Proliferation," *Exp. Eye Res.* 66: 581–589, 1998.

O'Neill et al., "Ribozyme–Based Therapeutic Approaches for Autosomal Dominant Retiniti Pigmentosa," *Investigative Ophthalmology & Visual Science* 41(10): 2863–2869, Sep. 2000.

Probst, J., "Antisense Oligodeoxynucleotide and Ribozyme Design," *Methods* 22: 271–281, 2000.

Kuang–Yu Jen and Alan M. Gerwirtz, "Suppression of Gene Expression by Targeted Disruption of Messenger RNA: Available Options and Current Strategies," *Stem Cells* 18:307–319, 2000.

* cited by examiner

EFFECT OF TREATMENT WITH CHIMERIC RIBOZYME ON SCARRING IN THE PORCINE SKIN MODEL

Panel A

Panel B

RIBOZYME THERAPY FOR THE TREATMENT OF PROLIFERATIVE SKIN AND EYE DISEASES

CROSS REFERENCE TO RELATED APPLICATION

This application claims the benefit of U.S. Provisional Patent Application No. 60/161,532 filed Oct. 26, 1999, where this provisional application is incorporated herein by reference in its entirety.

TECHNICAL FIELD

The present invention relates generally to therapeutics, and more specifically, to compositions and methods which may be utilized in the treatment and/or prevention of proliferative skin and eye diseases such as psoriasis and proliferative retinopathy.

BACKGROUND OF THE INVENTION

Proliferative skin diseases such as psoriasis affect as many as 2 to 3% of the entire U.S. population, with more than 250,000 new cases being diagnosed each year. The cost of treating psoriasis in the United States alone is estimated to range between three and five billion dollars per year, thus representing a major health cost to the health care system. Although the cause of psoriasis is presently unknown, there is evidence which tends to suggest that it is a polygenetic autoimmune disorder.

Proliferative skin diseases such as psoriasis are characterized by itchy, inflamed, scaly lesions which bleed easily. Although there are a wide variety of topical treatments (e.g., coal tar preparations, steroid-based creams and ointments) and systemic treatments (e.g., ultraviolet radiation, PUVA, steroids, and chemotherapeutic agents such as methotrexate), at present there is no cure for psoriasis. Further, presently available treatments are generally unsatisfactory, in that remission rates are high and certain therapeutic regimens have potentially serious side effects.

Proliferative diseases of the eye such as proliferative diabetic retinopathy (PDR) affect as many as 700,000 in the U.S., with more than 65,000 new cases diagnosed each year. Annually, as many as 25,000 people go blind from the disorder, making it a leading cause of blindness among working-age Americans. The cost savings from successful intervention could be as high as 100 million dollars per year. The disease does not stem from a single retinal change. Rather, it may be triggered by a combination of biochemical, metabolic, and hematological abnormalities.

There are no early symptoms. There is no pain, no blurred vision, and no ocular inflammation. In fact, many people do not develop any visual impairment until the disease has advanced well into its proliferative stage. At this point, the vision that has been lost cannot be restored. Laser surgery, also called photocoagulation, is the only current therapy to treat PDR. At present there is no cure for this disease.

Scarring is a significant source of disfigurement, pain, and increased medical costs for affected patients. It is the result of abnormal events during wound healing that can result in tissue overgrowth characterized by hyperproliferation of fibroblasts and excessive deposition of matrix. In surgery, scar tissue formation and contraction is a major clinical problem. Likewise, scarring following accidental burning or other injuries or trauma often has serious results, causing impaired function and unsightly aesthetic effects. Currently, there are no satisfactory treatments to prevent scarring.

Thus, a need exists for an effective therapy to treat proliferative diseases (e.g., psoriasis, PDR and scarring). The present invention satisfies this need and further provides other related advantages as well.

SUMMARY OF THE INVENTION

Briefly stated, the present invention provides ribozymes and ribozyme delivery systems which are able to inhibit the mechanisms involved in proliferation of cells associated with proliferative skin and eye diseases such as psoriasis, PDR and scarring. Accordingly, the present invention ribozymes are provided which are suitable for treating scarring and proliferative diseases by inhibiting a cytokine involved in inflammation, a matrix metalloproteinase involved in extracellular matrix elaboration, a cyclin, a cell-cycle dependent kinase, a growth factor involved in cell cycle regulation, or a reductase.

Within one aspect of the invention, such methods generally comprise the step of administering to a patient a therapeutically effective amount of ribozyme which cleaves RNA encoding a cytokine involved in inflammation, a matrix metalloproteinase, a cyclin, a cell-cycle dependent kinase, a growth factor, or a reductase such that said proliferative skin disease is treated. Within a related aspect, methods of treating proliferative skin disease are provided comprising the step of administering to a patient an effective amount of nucleic acid molecule comprising a promoter operably linked to a nucleic acid segment encoding a ribozyme which cleaves RNA encoding a cytokine involved in inflammation, a matrix metalloproteinase, a cyclin, a cell-cycle dependent kinase, a growth factor, or a reductase such that said proliferative skin disease is treated. Representative examples of proliferative skin diseases include psoriasis, atopic dermatitis, actinic keratosis, squamous or basal cell carcinoma, viral or seborrheic wart.

Within other aspects, such methods generally comprise the step of administering to a patient a therapeutically effective amount of ribozyme which cleaves RNA encoding a cytokine involved in inflammation, a matrix metalloproteinase, a cyclin, a cell-cycle dependent kinase, or a growth factor such that said proliferative eye disease is treated. Within a related aspect, methods of treating proliferative eye disease are provided comprising the step of administering to a patient an effective amount of nucleic acid molecules comprising a promoter operably linked to a nucleic acid segment encoding a ribozyme which cleaves RNA encoding a cytokine involved in inflammation, a matrix metalloproteinase, a cyclin, a cell-cycle dependent kinase, a growth factor, or a reductase such that said proliferative eye disease is treated. Representative examples of proliferative eye diseases include proliferative diabetic retinopathy, proliferative vitreoretinopathy, proliferative sickle cell retinopathy, retinopathy of prematurity and retinal detachment.

Within other aspects, methods are provided for treating or preventing scarring, comprising administering to a patient a therapeutically effective amount of ribozyme which cleaves RNA encoding a cytokine involved in inflammation, a matrix metalloproteinase, a cyclin, a cell-cycle dependent kinase, a growth factor, or a reductase such that said scarring is treated or prevented. Within another related aspect, methods are provided for treating or preventing scarring, comprising administering to a patient an effective amount of nucleic acid molecule comprising a promoter operably linked to a nucleic acid segment encoding a ribozyme which cleaves RNA encoding a cytokine involved in inflammation, a matrix metalloproteinase, a cyclin, a cell-cycle dependent kinase, a growth factor, or a reductase such that said scarring is treated or prevented. Representative examples of diseases or injuries which cause scarring include keloids, adhesions (e.g., surgical adhesions), hypertrophic burn scars, and trauma (e.g., blunt trauma or surgical trauma).

Cyclins and cell-cycle dependent kinases are directly involved in the check point control of cell division leading to proliferation. Particularly preferred cyclins or cell-cycle dependent kinases include CDK1, CDK2, CDK4, Cyclin B1, Cyclin D and PCNA.

Infection or injury induces a complex cascade of events including activation of the clotting pathway, adherence of immune cells to the endothelium, induction of proliferation and migration of cells into the injury site to rapidly repair the insult. These responses are mediated by certain cytokines and growth factors released from the injured tissue and by hematopoetic cells. Chronic inflammation develops when cytokines and growth factors continue to be produced, resulting in an exaggerated healing response. Particularly preferred cytokines include the inflammatory cytokines interleukin 1 alpha and beta, interleukin 2, interleukin 6, interleukin 8, interferon gamma, and tumor necrosis factor. Particularly preferred growth factors include vascular endothelial growth factor (VEGF), and platelet derived growth factor (PDGF).

Matrix metalloproteinases, along with their corresponding inhibitors, tissue inhibitors of metalloproteinases or TIMP, are involved in the repair of injured tissue. The balance between the proteinases and the inhibitors regulates the pattern and extent of wound healing. Excessive production of MMP or insufficient production of TIMP results in abnormal wound healing. Particularly preferred matrix metalloproteinases include MMP 1, MMP 2, MMP 3 and MMP 9.

Preferably, the ribozyme is a hammerhead or hairpin ribozyme, representative examples of which recognize the target site sequences set forth below and in the Examples. In preferred embodiments, the present invention also provides nucleic acid molecule encoding such ribozymes; further preferably, the nucleic acid is DNA or cDNA. Even further preferably, the nucleic acid molecule is under the control of a promoter to transcribe the nucleic acid.

In one embodiment of the invention, nucleic acid molecules are described which encode the ribozymes provided herein. Preferably, the vector is a plasmid, a virus, retrotransposon, a cosmid or a retrovirus. In one embodiment where the vector is a retroviral vector, the nucleic acid molecule encoding the ribozyme under the control of a promoter, which is preferably a pol III promoter, further preferably a human tRNA$^{Val}$ promoter or an adenovirus VAl promoter, is inserted between the 5' and 3' long terminal repeat sequences of the retrovirus.

These and other aspects of the present invention will become evident upon reference to the following detailed description and attached drawings. In addition, various references are set forth herein that describe in more detail certain procedures or compositions (e.g., plasmids, etc.), and are therefore incorporated by reference in their entirety as if each were individually noted for incorporation.

BRIEF DESCRIPTION OF THE DRAWINGS

FIG. 14A shows the dimensions of the wound (approximately 3 cm long, 5 mm deep and 6 mm wide). FIG. 14B shows excision of the skin and closure with a single suture.

DETAILED DESCRIPTION OF THE INVENTION

Definitions

Figure 1:
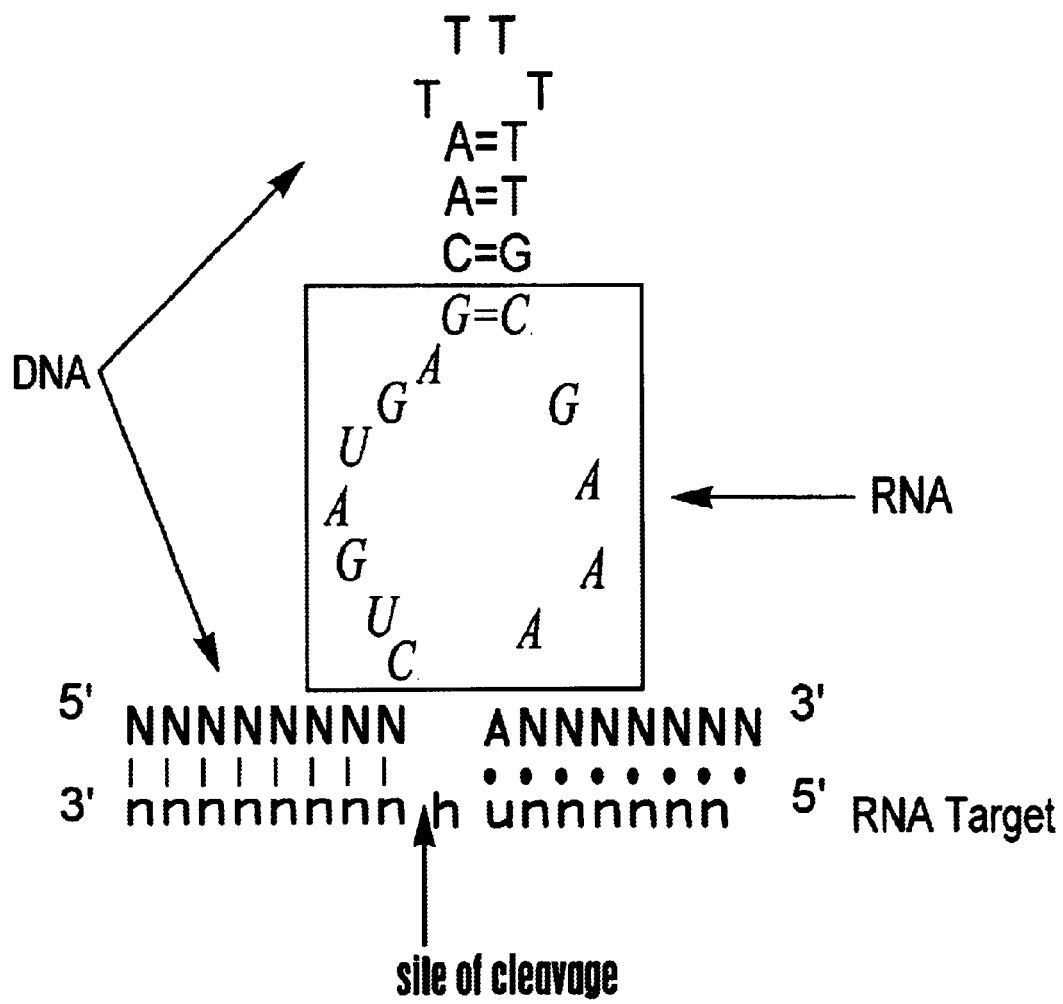
FIG. 1 is a schematic illustration of which shows the general structure of a chimeric DNA/RNA ribozyme (SEQ ID NOs: 4385 and 4386).

Prior to setting forth the invention, it may be helpful to an understanding thereof to first set forth definitions of certain terms that will be used hereinafter.

"Ribozyme" refers to a nucleic acid molecule which is capable of cleaving a specific nucleic acid sequence. Ribozymes may be composed of RNA, DNA, nucleic acid analogues (e.g., phosphorothioates), or any combination of these (e.g., DNA/RNA chimerics). Within particularly preferred embodiments, a ribozyme should be understood to refer to RNA molecules that contain anti-sense sequences for specific recognition, and an RNA-cleaving enzymatic activity.

"Ribozyme gene" refers to a nucleic acid molecule (e.g., DNA) consisting of the ribozyme sequence which, when transcribed into RNA, will yield the ribozyme.

"Vector" refers to an assembly which is capable of expressing a ribozyme of interest. The vector may be composed of either deoxyribonucleic acids ("DNA") or ribonucleic acids ("RNA"). Optionally, the vector may include a polyadenylation sequence, one or more restriction sites, as well as one or more selectable markers such as neomycin phosphotransferase, hygromycin phosphotransferase or puromycin-N-acetyl-transferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

"Nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (such as deoxyribonucleotides and ribonucleotides), or analogs of naturally-occurring nucleotides (e.g., α-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

"Isolated nucleic acid molecule" is a nucleic acid molecule that is not integrated in the genomic DNA of an organism. For example, a DNA molecule that encodes a gene that has been separated from the genomic DNA of a eukaryotic cell is an isolated DNA molecule. Another example of an isolated nucleic acid molecule is a chemically-synthesized nucleic acid molecule that is not integrated in the genome of an organism.

"Promoter" is a nucleotide sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

As noted above, proliferative diseases such as psoriasis, PDR, and scarring affect many individuals and represent a major cost to the health care system. As discussed in more detail below, by interfering with cell-cycle control of cells which might otherwise proliferate, proliferative diseases such as psoriasis or PDR can be effectively treated. This invention accomplishes such by providing ribozymes and methods of using ribozymes that inhibit the activity of cytokines which are involved in inflammation, matrix metalloproteinases, cyclins, cell-cycle dependent kinases, growth factors, reductases, all of which directly or indirectly contribute to proliferation.

Cyclins and cell-cycle dependent kinases are directly involved in the signaling and synthesis that results in cells progressing through the cell cycle to replicate. Representative examples of suitable ribozyme targets include cdk1 ribozyme binding sites (SEQ ID NOS: 1–149); cdk2 ribozyme binding sites (SEQ ID NOS: 150–3010); cdk3 ribozyme binding sites (SEQ ID NOS: 302–405); cdk4 ribozyme binding sites (SEQ ID NOS: 406–526); cdk6 ribozyme binding sites (SEQ ID NOS: 527–665); cdk7 ribozyme binding sites (SEQ ID NOS: 666–866); cdk8 ribozyme binding sites (SEQ ID NOS: 867–1112); cdk-wehu ribozyme binding sites (SEQ ID NOS: 1113–1408); cyclin A2 ribozyme binding sites (SEQ ID NOS: 1409–1614); cyclin C ribozyme binding sites (SEQ ID NOS: 1615–1819); cyclin D1 ribozyme binding sites (SEQ ID NOS: 1820–1889); cyclin D2 ribozyme binding sites (SEQ ID NOS: 1890–1975); cyclin D3 ribozyme binding sites (SEQ ID NOS: 1976–2053); cyclin E ribozyme binding sites (SEQ ID NOS: 2054–2318); cyclin F ribozyme binding sites (SEQ ID NOS: 2319–2561); cyclin G1 ribozyme binding sites (SEQ ID NOS: 2562–2787); cyclin H ribozyme binding sites (SEQ ID NOS: 2788–2964); cyclin A1 ribozyme binding sites (SEQ ID NOS: 2965–3257); cyclin B1 ribozyme binding sites (SEQ ID NOS: 3258–3478) ; cdc25 hs ribozyme binding sites (SEQ ID NOS: 3479–3854); PCNA HH ribozyme binding sites (SEQ ID NOS: 3855–4115); and chimeric hairpin ribozymes: SEQ ID NOS: 4116–4119).

As noted above, infection or injury induces a complex cascade of events including activation of the clotting pathway, adherence of immune cells to the endothelium, induction of proliferation and migration of cells into the injury site to rapidly repair the insult. These responses are mediated by certain cytokines and growth factors released from the injured tissue and by hematopoetic cells. Chronic inflammation develops when cytokines and growth factors continue to be produced, resulting in an exaggerated healing response. Particularly preferred cytokines include the inflammatory cytokines interleukin 1 alpha and beta, interleukin 2, interleukin 6, interleukin 8, interferon gamma, and tumor necrosis factor. Particularly preferred growth factors include vascular endothelial growth factor (VEGF), and platelet derived growth factor (PDGF).

Matrix metalloproteinases, along with their corresponding inhibitors, tissue inhibitors of metalloproteinases or TIMP, are involved in a the repair of injured tissue. The balance between the proteinases and the inhibitors regulates the pattern and extent of wound healing. Excessive production of MMP or insufficient production of TIMP results in abnormal wound healing. Particularly preferred-matrix metalloproteinases include MMP 1, MMP 2, MMP 3 and MMP 9.

Ribozymes

As noted above, the present invention provides ribozymes having the ability to cleave or otherwise inhibit nucleic acid molecules which are either directly, or indirectly (e.g., they encode proteins) involved in cell-cycle control. Several different types of ribozymes may be constructed for use within the present invention, including for example, hammerhead ribozymes (Rossi, J. J. et al., *Pharmac. Ther.* 50:245–254, 1991) (Forster and Symons, *Cell* 48:211–220, 1987; Haseloff and Gerlach, *Nature* 328:596–600, 1988; Walbot and Bruening, *Nature* 334:196, 1988; Haseloff and Gerlach, *Nature* 334:585, 1988; Haseloff et al., U.S. Pat. No. 5,254,678), hairpin ribozymes (Hampel et al., *Nucl. Acids Res.* 18:299–304, 1990, and U.S. Pat. No. 5,254,678), hepatitis delta virus ribozymes (Perrotta and Been, *Biochem.* 31:16, 1992), Group I intron ribozymes (Cech et al., U.S. Pat. No. 4,987,071) and RNase P ribozymes (Takada et al., *Cell* 35:849, 1983); (see also, WO 95/29241, entitled "Ribozymes with Product Ejection by Strand Displacement"; and WO 95/31551, entitled "Novel Enzymatic RNA Molecules."

Cech et al. (U.S. Pat. No. 4,987,071, issued Jan. 22, 1991) has disclosed the preparation and use of ribozymes which are based on the properties of the Tetrahymena ribosomal RNA self-splicing reaction. These ribozymes require an eight base pair target site and free guanosine (or guanosine derivatives). A temperature optimum of 50° C. is reported for the endoribonuclease activity. The fragments that arise from cleavage contain 5'-phosphate and 3'-hydroxyl groups and a free guanosine nucleotide added to the 5'-end of the cleaved RNA.

In contrast to the ribozymes of Cech et al., particularly preferred ribozymes of the present invention hybridize efficiently to target sequences at physiological temperatures, making them suitable for use in vivo, and not merely as research tools (see column 15, lines 18 to 42, of Cech et al., U.S. Pat. No. 4,987,071). Thus, particularly preferred ribozymes for use within the present invention include hairpin ribozymes (for example, as described by Hampel et al., European Patent Publication No. 0 360 257, published Mar. 26, 1990) and hammerhead ribozymes. Briefly, the sequence requirement for the hairpin ribozyme is any RNA sequence consisting of NNNBN*GUC (N)λ (Sequence ID Nos. 4120–4124) (where x is any number from 6 to 10, N*G is the cleavage site, B is any of G, C, or U, and N is any of G, U, C, or A). Representative examples of recognition or target sequences for hairpin ribozymes are set forth below in the Examples. Additionally, the backbone or common region of the hairpin ribozyme can be designed using the nucleotide sequence of the native hairpin ribozyme (Hampel et al., *Nucl. Acids Res.* 18:299–304, 1990) or it can be modified to include a "tetraloop" structure that increases stability and catalytic activity (see Example 2; see also Yu et al., *Virology* 206:381–386, 1995; Cheong et al., *Nature* 346:680–682, 1990; Anderson et al., *Nucl. Acids Res.* 22:1096–1100, 1994).

The sequence requirement at the cleavage site for the hammerhead ribozyme is any RNA sequence consisting of NUH (where N is any of G, U, C, or A and H represents C, U, or A) can be targeted. Accordingly, the same target within the hairpin leader sequence, GUC, is useful for the hammerhead ribozyme. The additional nucleotides of the hammerhead ribozyme or hairpin ribozyme is determined by the target flanking nucleotides and the hammerhead consensus sequence (see Ruffner et al., *Biochemistry* 29:10695–10702, 1990). This information, along with the sequences and disclosure provided herein, enables the production of hairpin ribozymes of this invention.

The ribozymes of this invention, as well as DNA encoding such ribozymes and other suitable nucleic acid molecules, described in more detail below, can be chemically synthesized using methods well known in the art for the synthesis of nucleic acid molecules (see e.g., Heidenreich et al., *J FASEB* 70(1):90–6, 1993; Sproat, *Curr. Opin. Biotechnol.* 4(1):20–28, 1993). Alternatively, commercial suppliers such as Promega, Madison, Wis., USA, provide a series of protocols suitable for the production of nucleic acid molecules such as ribozymes.

Within one aspect of the present invention, ribozymes are prepared from a DNA molecule or other nucleic acid molecule (which, upon transcription, yields an RNA molecule operably linked to an RNA polymerase promoter, e.g., the promoter for T7 RNA polymerase or SP6 RNA polymerase. Accordingly, also provided by this invention are nucleic acid molecules, e.g., DNA or cDNA, coding for the ribozymes of this invention. When the vector also contains an RNA polymerase promoter operably linked to the DNA molecule, the ribozyme can be produced in vitro upon incubation with the RNA polymerase and appropriate nucleotides. In a separate embodiment, the DNA may be inserted into an expression cassette, such as described in Cotten and Birnstiel, *EMBO J.* 8(12):3861–3866, 1989, and in Hempel et al., *Biochemistry* 28:4929–4933, 1989. A more detailed discussion of molecular biology methodology is disclosed in Sambrook et al., *Molecular Cloning: A Laboratory Manual*, Cold Spring Harbor Press, 1989.

During synthesis, the ribozyme can be modified by ligation to a DNA molecule having the ability to stabilize the ribozyme and make it resistant to RNase (Rossi et al., *Pharmac. Ther.* 50:245–254, 1991). In another embodiment, the ribozyme can be modified to a phosphothio-analog for use in liposome delivery systems. This modification also renders the ribozyme resistant to endonuclease activity. In yet another embodiment, the ribozyme can be modified to contain propanediol linkages or to incorporate 2'-O-methylated nucleotides.

Vectors

Use of ribozymes to treat proliferative skin diseases such as psoriasis or eczema involves introduction of functional ribozyme to the infected cell of interest. This can be accomplished by either synthesizing functional ribozyme in vitro prior to delivery, or, by delivery of DNA capable of driving ribozyme synthesis in vivo.

More specifically, within other aspects of the invention the ribozyme gene may be constructed within a vector which is suitable for introduction to a host cell (e.g., prokaryotic or eukaryotic cells in culture or in the cells of an organism). Appropriate prokaryotic and eukaryotic cells can be transfected with an appropriate transfer vector containing the nucleic acid molecule encoding a ribozyme of this invention.

To produce the ribozymes with a vector in vivo, nucleotide sequences coding for ribozymes are preferably placed under the control of a eukaryotic promoter such as pol III (e.g., tRNA or VA-1 from adenovirus), CMV, SV40 late, or SV40 early promoters. Within certain embodiments, the promoter may be a tissue or cell-specific promoter. Ribozymes may thus be produced directly from the transfer vector in vivo.

A wide variety of vectors may be utilized within the context of the present invention, including for example, plasmids, viruses, retrotransposons and cosmids. Representative examples include adenoviral vectors (e.g., WO 94/26914, WO 93/9191; Yei et al., *Gene Therapy* 1:192–200, 1994; Kolls et al., *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J. Neurosci.* 5(10):1287–1291, 1993), adeno-associated type 1 ("AAV-1") or adeno-associated type 2 ("AAV-2") vectors (see WO 95/13365; Flotte et al., *PNAS* 90(22):10613–10617, 1993), hepatitis delta vectors, live, attenuated delta viruses and herpes viral vectors (e.g., U.S. Pat. No. 5,288,641), as well as vectors which are disclosed within U.S. Pat. No. 5,166,320. Other representative vectors include retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218). General methods of using such vectors in gene therapy are well known in the art (see, for example, Larrick, J. W. and Burck, K. L., *Gene Therapy Application of Molecular Biology*, Elsevier Science Publishing Co., Inc., New York, N.Y., 1991 and Kreigler, M., *Gene Transfer and Expression; A Laboratory Manual*, W.H. Freeman and Company, New York, 1990).

Further provided by this invention are vectors having more than one nucleic acid molecule encoding a ribozyme of this invention, each molecule under the control of a separate eukaryotic promoter (or, an Internal Ribosome Entry Site or "IRES") or alternatively, under the control of single eukaryotic promoter. Representative examples of other nucleic acid molecules which may be delivered by the vectors of the present invention include therapeutic molecules such as interferon (e.g., alpha, beta or gamma), as well as a wide variety of other cytokines or growth factors, and facilitators which assist or aid ribozymes in cleaving a target sequence by unwinding or otherwise limiting secondary folding which might otherwise inhibit the ribozyme. These vectors provide the advantage of providing multi-functional therapy against Psoriasis, preferably with the various therapies working together in synergy.

Host prokaryotic and eukaryotic cells stably harboring the vectors described above also are provided by this invention. Suitable host cells include bacterial cells, rat cells, mouse cells, and human cells.

Delivery

Within certain aspects of the invention, ribozyme molecules, or nucleic acid molecules which encode the ribozyme, may be introduced into a host cell or administered to a patient utilizing a vehicle, or by various physical methods. Representative examples of such methods include transformation using calcium phosphate precipitation (Dubensky et al., *PNAS* 81:7529–7533, 1984), direct microinjection of such nucleic acid molecules into intact target cells (Acsadi et al., *Nature* 352:815–818, 1991), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al., *PNAS* 89:6094, 1990), lipofection (Felgner et al., *Proc. Natl. Acad. Sci. USA* 84:7413–7417, 1989), microprojectile bombardment (Williams et al., *PNAS* 88:2726–2730, 1991), polycation compounds such as polylysine, receptor specific ligands, liposomes entrapping the nucleic acid molecules, spheroplast fusion whereby *E. coli* containing the nucleic acid molecules are stripped of their outer cell walls and fused to animal cells using polyethylene glycol, viral transduction, (Cline et al., *Pharmac. Ther.* 29:69, 1985; and Friedmann et al., *Science* 244:1275, 1989), and DNA ligand (Wu et al, *J. of Biol. Chem.* 264:16985–16987, 1989). In one embodiment, the ribozyme is introduced into the host cell using a liposome.

Within further embodiments of the invention, additional therapeutic molecules (e.g., interferon) or facilitators may be delivered utilizing the methods described herein. Such delivery may be either simultaneous to, or before or after the delivery of a ribozyme or vector expressing ribozymes.

Pharmaceutical Compositions

As noted above, pharmaceutical compositions (or "medicaments") also are provided by this invention. These compositions contain any of the above described ribozymes, DNA molecules, vectors or host cells, along with a pharmaceutically or physiologically acceptable carrier, excipient, or, diluent. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Particularly preferred carriers include cholesterols such as DOTAP: cholesterol.

Additional ingredients added to the compositions for the express purpose of inhibiting endogenous ribonucleases include reducing agents such as dithiothreitol, detergents such as sodium dodecyl sulfate, and other agents such as vanidyl nucleotides, aurin tricarbocylic acid, hydrogen peroxide and RNA decoys such as tRNA.

Pharmaceutical compositions of the present invention may also be prepared to contain, or express (e.g., if a vector), one or more additional therapeutic molecules (e.g., interferon) or facilitators.

The pharmaceutical compositions of the present invention may be prepared for administration by a variety of different routes, including for example, topically, intradermally, or intraocullarly. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

Pharmaceutical compositions of the present invention are useful for both diagnostic and therapeutic purposes.

Therapeutic Methods

Methods of treating proliferative diseases such as psoriasis or PDR are also provided by this invention. More specifically, within one aspect of the present invention proliferative diseases such as psoriasis or PDR may be treated by administering to a warm-blooded animal (e.g., a human) a therapeutically effective amount of ribozyme, and/or, nucleic acid molecule or vector which encodes the ribozyme.

Briefly, cells in response to injury or other insult typically follow at least one of two possible pathways: normal wound healing or exaggerated growth. For normal wound healing accelerated growth and maturation of cells occurs in order to allow healing of the wound as soon as possible.

Proliferative diseases such as psoriasis, scarring and PDR are similar in many respects to the process of wound healing. Namely, cells are created and migrate in a relatively short period of time. However, if the proliferation is too rapid or the signals to proliferate continue for too long a period of time, the cells build up to form thickened lesions. This growth is supported by new blood vessels, as well as the infiltration of a variety of lymphocytes which produce a wide variety of growth factors (that further increases the proliferation of the cells). These cells can produce tissue degrading enzymes which cause the destruction of surrounding tissue. In some cases, the thickened lesions contract, distorting the surface of the skin or retina. The result of the exaggerated growth is the clinical symptoms associated with the proliferative disease.

The present invention provides the treatment of proliferative skin and eye diseases by contacting desired cells with an effective amount of ribozyme of this invention or, alternatively, by transducing the cell with an effective amount of vector having a nucleic acid molecule encoding the ribozyme. A suitable "therapeutically effective amount" will depend on the nature and extent of diseased tissue being treated, or, if a medical procedure is contemplated in which abnormal proliferation can be expected, prevented. Such "therapeutically effective amounts" can be readily determined by those of skill in the art using well known methodology, and suitable animal models (e.g. a rat, rabbit, or porcine model), or, based upon clinical trials. As utilized herein, a patient is deemed to be "treated" if the proliferative skin or eye disease is reversed or inhibited in a patient in a quantifiable manner. Further, a therapeutically effective amount or regimen of treatment should result in: (1) decrease in the frequency, severity, or, duration of clinical symptoms (e.g., inflammation, thickening of the tissue, contraction, scaling, "burning", or itching); (2) increase of time in the period of remission; (3) a change in pathological symptoms (e.g., inhibition of keratinocyte, fibroblast, glia, or retinal pigment epithelium proliferation); (4) prevention of retinal detachment; and/or (5) prevention of visual impairment.

When exogenously delivering the ribozyme, the RNA molecule can be embedded within a stable RNA molecule or in another form of protective environment, such as a liposome. Alternatively, the RNA can be embedded within RNase-resistant DNA counterparts. Cellular uptake of the exogenous ribozyme can be enhanced by attaching chemical groups to the DNA ends, such as cholesteryl moieties (Letsinger et al., P.N.A.S., U.S.A., 1989).

In another aspect of the invention, the target cell is transduced under conditions favoring insertion of the vector into the target cell and stable expression of the nucleic acid encoding the ribozyme. The target cell can include but is not limited to cells found in the skin basal level, dermis, or epidermis; the vitreous of the eye, and the retinal and pigment epithelium layers of the eye.

In addition, the ribozyme, ribozyme gene or vector may be readily incorporated into a biodegradable polymer, sphere, pleuroinc gel, or the like to aid incorporation into cells.

The ribozyme (or nucleic acid molecule or vector encoding the ribozyme) can be administered in any manner sufficient to achieve the above therapeutic results, but preferred methods include topical and systemic administration. Patients with localized disease can be administered ribozymes (or a nucleic acid molecule or vector) in a topical cream, ointment or emollient applied directly to skin lesions. For example, a topical cream containing 100 milligrams ribozymes by weight can be administered depending upon severity of the disease and the patient's response to treatment. In a preferred embodiment, a topical preparation containing ribozymes 100 milligrams by weight would be administered to psoriatic lesions. Alternatively, direct intracutaneous or intraocular injection of ribozymes in a suitable pharmaceutical vehicle can be used for the management of individual lesions.

The ribozyme may be formulated along with a liquid (e.g., DOTAP: cholesterol). In addition, the ribozyme may be formulated with ribonuclease inhibitors, including, but not limited to, reducing agent (e.g., dithiothreitol), detergent (e.g., sodium dodecyl sulfate), vanidyl nucleotides, aurin tricarboxcylic acid, hydrogen peroxide, and RNA decoys (e.g., tRNAs).

The following examples are offered by way of illustration, and not by way of limitation.

EXAMPLES

Example 1

Criteria for Ribozume Site Selection

A. Selection of Sites for Hairpin Ribozymes

Hairpin ribozymes suitable for use within the present invention preferably recognize the following sequence of RNA: NNNBNGUCNNNNNNNN (SEQ ID NO: 4122) wherein the ribozyme is constructed so as to be complementary to the underlined sequences, and wherein B is C, G or U. The sequence GUC must be conserved for all hairpin ribozymes described below. Other nucleotides ("N" as underlined above) preferably have a high degree of sequence conservation in order to limit the need for multiple ribozymes against the same target site.

B. Selection of Cleavage Sites for Hammerhead Ribozymes

Hammerhead ribozymes suitable for use within the present invention preferably recognize the sequence NUH, wherein N is any of G, U, C, or A and H is C, U, or A. The hairpin recognition sites GUC are a subset of the hammerhead recognition sites NUH. Therefore, all hairpin sites are by definition also hammerhead sites, although the converse is not true. Representative GUC hairpin/hammerhead ribozyme recognition sites for various genes are provided below in Tables 1–16. Hammerhead only sites are shown in Table 18.

TABLE 1

Hairpin/Hammerhead Ribozyme Recognition Sites for cdc 2 kinase

| NUCL. POS. | SEQUENCE (5' to 3') | I.D. No. |
|---|---|---|
| 175 | ACTTCGTCATCCAAAT | 4125 |
| 189 | ATATAGTCAGTCTTCA | 4126 |
| 193 | AGTCAGTCTTCAGGAT | 4127 |
| 289 | TCCTGGTCAGTACATG | 4128 |
| 355 | GTTTTGTCACTCTAGA | 4129 |
| 530 | CTGGGGTCAGCTCGTT | 4130 |

TABLE 2

Hairpin/Hammerhead Ribozyme Recognition Sites for Cyclin B1

| NUCL. POS. | SEQUENCE (5' to 3') | I.D. No. |
|---|---|---|
| 13 | TCCGAGTCACCAGGAA | 4131 |
| 282 | CCAGTGTCTGAGCCAG | 4132 |
| 428 | CCTGTGTCAGGCTTTC | 4133 |
| 559 | AAGCAGTCAGACCAAA | 4134 |
| 581 | ACTGGGTCGGGAAGTC | 4135 |
| 679 | TGACTGTCTCCATTAT | 4136 |
| 745 | TTGGTGTCACTGCCAT | 4137 |
| 887 | CTTTGGTCTGGGTCGG | 4138 |
| 893 | TCTGGGTCGGCCTCTA | 4139 |
| 1107 | TACCTGTCATATACTG | 4140 |
| 1162 | ATGTAGTCATGGTAAA | 4141 |
| 1198 | TGACTGTCAAGAACAA | 4142 |

TABLE 3

Hairpin/Hammerhead Ribozyme Recognition Sites for PCNA

| UCL. POS. | SEQUENCE (5' to 3') | I.D. No. |
|---|---|---|
| −131 | GAGTGGTCGTTGTCTT | 4143 |
| −125 | TCGTTGTCTTTCTAGG | 4144 |
| 19 | GCCTGGTCCAGGGCTC | 4145 |
| 126 | GACTCGTCCCACGTCT | 4146 |
| 159 | CTGCGGTCTGAGGGCT | 4147 |
| 546 | AAATTGTCACAGACAA | 4148 |
| 868 | TTTCTGTCACCAAATT | 4149 |
| 983 | ATCTGGTCTAGTTAAC | 4150 |
| 1008 | TTTTTGTCTCTTAGAA | 4151 |
| 1047 | AAAGGGTCTTGACTCT | 4152 |

TABLE 4

Hairpin/Hammerhead Ribozyme Recognition Sites for MMP-1

| NUCL. POS. | SEQUENCE (5' to 3') | I.D. No. |
|---|---|---|
| 48 | GTGG TGTC TCACAGCT | 4389 |
| 301 | AGTT TGTC CTCACTGA | 4390 |
| 454 | CCAA GGTC TCTGAGGG | 4391 |
| 464 | TGAG GGTC AAGCAGAC | 4392 |
| 799 | ATCC TGTC CAGCCCAT | 4393 |
| 1446 | TGTG AGTC CAAAGAAG | 4394 |
| 1475 | GAAC TGTC TATTTTCT | 4395 |
| 1488 | TCTC AGTC ATTTTTAA | 4396 |
| 1507 | CTAG AGTC ACTGATAC | 4397 |
| 1766 | CATG AGTC TTTGCCGG | 4398 |

TABLE 5

Hairpin/Hammerhead Ribozyme Recognition Sites for IL-1 beta

| UCL. POS. | SEQUENCE (5' to 3') | I.D. No. |
|---|---|---|
| 13 | caag tgtctgaagcag | 4399 |
| 195 | gccg cgtcagttgttg | 4400 |
| 408 | gtga tgtctggtccat | 4401 |
| 413 | gtct ggtccatatgaa | 4402 |
| 480 | tcca tgtcctttgtac | 4403 |
| 555 | tacc tgtcctgcgtgt | 4404 |
| 646 | gatt tgtcttcaacaa | 4405 |
| 687 | tttg agtctgcccagt | 4406 |
| 782 | tgcc cgtcttcctggg | 4407 |
| 801 | tttg tgtcttcctaaa | 4408 |
| 830 | agag agtcctgtgctg | 4409 |
| 921 | ctgt tgtctacaccaa | 4410 |

TABLE 6

Hairpin/Hammerhead Ribozyme Recognition Sites for VEGF

| UCL. POS. | SEQUENCE (5' to 3') | I.D. No. |
|---|---|---|
| 83 | CTGCTgtcTTGGGTGC | 4411 |
| 136 | AAGTGgtcCCAGGCTG | 4412 |
| 364 | GAGGAgtcCAACATCA | 4413 |

TABLE 7

Hairpin/Hammerhead Ribozyme Recognition Sites for IL2

| UCL. POS. | SEQUENCE (5' to 3') | I.D. No. |
|---|---|---|
| 68 | caactcctgcttgcattgca | 4414 |
| 96 | ttgcacttgtcacaaacagta | 4415 |
| 289 | gcttcagtgtctagaagaaga | 4416 |
| 450 | taccttttgtcaaagcatcat | 4417 |

TABLE 8

Hairpin/Hammerhead Ribozyme Recognition Sites for IFN gamma

| UCL. POS. | SEQUENCE (5' to 3') | I.D. No. |
|---|---|---|
| 246 | gccaaattgtctcttttact | 4418 |
| 458 | gctgaatgtcgccagcagct | 4419 |
| 493 | aaaaaggagtcagatgctgt | 4420 |
| 534 | gtaatggttgtcctgcctgcaa | 4421 |
| 718 | ctgtgactgtctcacttaatc | 4422 |
| 958 | ttgaatgtgtcaggtgaccct | 4423 |

TABLE 9

Hairpin/Hammerhead Ribozyme Recognition Sites for IL1 alpha

| UCL. POS. | SEQUENCE (5' to 3') | I.D. No. |
|---|---|---|
| 19 | GCGTTTGAGTCAGCAAAGAAG | 4424 |
| 120 | GATCATCTGTCTCTGAATCAG | 4425 |
| 192 | CAATCTGTGTCTCTGAGTATC | 4426 |
| 860 | GGTCTGGAGTCTCACTTGTCT | 4427 |
| 869 | TCTCACTTGTCTCACTTGTGC | 4428 |
| 938 | TACTGTTAGTCATTTGCTGAG | 4429 |
| 1624 | GCATTTTGGTCCAAGTTGTGC | 4430 |
| 1729 | AGTAATTGGTCCGATCTTTGA | 4431 |
| 1921 | CCGTGCTGGTCTCGAACTTCT | 4432 |
| 2063 | AATCCTCAGTCAGCCGTGTTT | 4433 |
| 2404 | TTCTTGTCCCAAATAAAA | 4434 |

TABLE 10

Hairpin/Hammerhead Ribozyme Recognition Sites for IL6

| NUCL. POS. | SEQUENCE (5' to 3') | I.D. No. |
|---|---|---|
| 79 | CGCCTTCGGTCCAGTTGCCTT | 4435 |
| 403 | CATCACTGGTCTTTTGGAGTT | 4436 |
| 659 | TTCCTGCAGTCCAGCCTGAGG | 4437 |
| 736 | TTCTTCTGGTCAGAAACCTGT | 4438 |
| 747 | AGAAACCTGTCCACTGGGCAC | 4439 |

TABLE 11

Hairpin/Hammerhead Ribozyme Recognition Sites for IL8

| NUCL. POS. | SEQUENCE (5' to 3') | I.D. No. |
|---|---|---|
| 493 | ttgtgtgggtctgttgtaggg | 4440 |
| 832 | agagctctgtctggaccccaa | 4441 |
| 873 | caaccctagtctgctagccag | 4442 |

TABLE 12

Hairpin/Hammerhead Ribozyme Recognition Sites for MMP2

| UCL. POS. | SEQUENCE (5' to 3') | I.D. No. |
|---|---|---|
| 46 | GCCGCGCCGTCGCCCATCATC | 4443 |
| 614 | GCCAAGTGGTCCGTGTGAAGT | 4444 |
| 774 | CGGCTTCTGTCCCCATGAAGC | 4445 |
| 1001 | CCCCCTGTGTCTTCCCCTTCA | 4446 |
| 1248 | GAACTTCCGTCTGTCCCAGGA | 4447 |
| 1252 | TTCCGTCTGTCCCAGGATGAC | 4448 |
| 1343 | TGGGCCCTGTCACTCCTGAGA | 4449 |
| 1811 | TGGATGCCGTCGTGGACCTGC | 4450 |
| 1832 | GGGCGGGGGTCACAGCTACTT | 4451 |
| 2312 | TGGAGACTGTCTCAAGAGGGC | 4452 |
| 2472 | TTCTTTGGGTCTTGTTTTTTT | 4453 |

TABLE 13

Hairpin/Hammerhead Ribozyme Recognition Sites for MMP3

| UCL. POS. | SEQUENCE (5' to 3') | I.D. No. |
|---|---|---|
| 8 | atgaagagtcttccaatcct | 4454 |
| 173 | ggacagtggtcctgttgttaa | 4455 |
| 293 | tgacgttggtcacttcagaac | 4456 |
| 674 | ctccctgggtctctttcactc | 4457 |
| 753 | ttccgcctgtctcaagatgat | 4458 |
| 780 | ggcattcagtccctctatgga | 4459 |
| 838 | cggaacctgtccctccagaac | 4460 |
| 882 | cctgctttgtccttttgatgct | 4461 |
| 895 | ttgatgctgtcagcactctga | 4462 |

TABLE 14

Hairpin/Hammerhead Ribozyme Recognition Sites for MMP9

| UCL. POS. | SEQUENCE (5' to 3') | I.D. No. |
|---|---|---|
| 41 | agccctggtcctggtgctcc | 4463 |
| 94 | cagcgccagtccacccttgtg | 4464 |
| 208 | cgtggagagtcgaaatctctg | 4465 |
| 253 | aagcaactgtccctgcccgag | 4466 |
| 320 | ggtgcggggtcccagacctgg | 4467 |
| 518 | cagacatcgtcatccagtttg | 4468 |
| 533 | agtttggtgtcgcggagcacg | 4469 |
| 649 | gagttgtggtccctgggcaag | 4470 |
| 665 | gcaagggcgtcgtggttccaa | 4471 |
| 762 | caccgacggtcgctccgacgg | 4472 |
| 936 | cacggacggtcgctccgacgg | 4473 |
| 1061 | agctgtgcgtcttcccccttca | 4474 |
| 1350 | cctctatggtcctcgccctga | 4475 |
| 1418 | ccccgacggtctgccccaccg | 4476 |
| 1442 | cccccactgtccacccctcag | 4477 |
| 1548 | gcctttgagtccggtggacga | 4478 |
| 1727 | tggactcggtctttgaggagc | 4479 |
| 1798 | acaggcgcgtcggtgctgggc | 4480 |
| 1818 | cccgaggcgtctggacaagct | 4481 |
| 2151 | gggctcccgtcctgctttgca | 4482 |

TABLE 15

Hairpin/Hammerhead Ribozyme Recognition Sites for PDGF A

| UCL. POS. | SEQUENCE (5' to 3') | I.D. No. |
|---|---|---|
| 29 | ccggccgggtcgctcctgaag | 4483 |
| 125 | cccctccgtccccaccccca | 4484 |
| 241 | cgggcgccgtccgccagctcc | 4485 |
| 494 | ggcccgcagtcagatccacag | 4486 |
| 589 | ctacggggtccatgcccacta | 4487 |
| 661 | aggaagctgtccccgctgtct | 4488 |
| 670 | tccccgctgtctgcaagacca | 4489 |
| 688 | ccaggacggtcatttacgaga | 4490 |
| 710 | tcctcggagtcaggtcgaccc | 4491 |
| 799 | cgagcagtgtcaagtgccagc | 4492 |
| 820 | cctcccgcgtccaccaccgca | 4493 |
| 835 | accgcagcgtcaaggtggcca | 4494 |
| 981 | cctagggagtcaggtaaaaaa | 4495 |
| 1140 | agtgtgcggtcttgttctcc | 4496 |
| 1168 | aaaactgtgtccgagaacact | 4497 |
| 1269 | gcttccttgtcaaaaagagag | 4498 |

TABLE 16

Hairpin/Hammerhead Ribozyme Recognition Sites for PDGF B

| UCL. POS. | SEQUENCE (5' to 3') | I.D. No. |
|---|---|---|
| 106 | aggttggagtccctgggcgc | 4499 |
| 437 | ggcccggagtcggcatgaatc | 4500 |

TABLE 16-continued

Hairpin/Hammerhead Ribozyme Recognition Sites for PDGF B

| UCL. POS. | SEQUENCE (5' to 3') | I.D. No. |
|---|---|---|
| 469 | ctcttcctgtctctctgctgc | 4501 |
| 489 | ctacctgcgtctggtcagcgc | 4502 |
| 494 | tgcgtctggtcagcgccgagg | 4503 |
| 893 | tgcgacctgtccaggtgagaa | 4504 |
| 1085 | cggtgcgagtccgccggcccc | 4505 |
| 1265 | tttccctcgtccgtctgtctc | 4506 |
| 1269 | cctcgtccgtcgtctcgatg | 4507 |
| 1273 | gtccgtctgtctcgatgcctg | 4508 |
| 1325 | ctccacgtgtccgtccaccct | 4509 |
| 1329 | acgtgtccgtccaccttcca | 4510 |
| 1349 | atcagcgggtctcctcccag | 4511 |
| 1476 | ctgatggggtcgctctttggg | 4512 |
| 1545 | tgtggactgtcctgaggagcc | 4513 |

TABLE 17

Further Ribozyme Recognition Sites

| TARGET SITE | I.D. No. |
|---|---|
| cdk1 ribozyme binding sites: | 1–149 |
| cdk2 ribozyme binding sites: | 150–301 |
| cdk3 ribozyme binding sites: | 302–405 |
| cdk4 ribozyme binding sites: | 406–526 |
| cdk6 ribozyme binding sites: | 527–665 |
| cdk7 ribozyme binding sites: | 666–866 |
| cdk8 ribozyme binding sites: | 867–1112 |
| cdk-we-hu ribozyme binding sites: | 1113–1408 |
| cyclin A2 ribozyme binding sites: | 1409–1614 |
| cyclin C ribozyme binding sites: | 1615–1819 |
| cyclin D1 ribozyme binding sites: | 1820–1889 |
| cyclin D2 ribozyme binding sites: | 1890–1975 |
| cyclin D3 ribozyme binding sites: | 1976–2053 |
| cyclin E ribozyme binding sites: | 2054–2318 |
| cyclin F ribozyme binding sites: | 2319–2561 |
| cyclin G1 ribozyme binding sites: | 2562–2787 |
| cyclin H ribozyme binding sites: | 2788–2964 |
| cyclin A1 ribozyme binding sites: | 2965–3257 |
| cyclin B1 ribozyme binding sites: | 3258–3478 |
| cdc25 hs ribozyme binding sites: | 3479–3854 |
| PCNA HH ribozyme binding sites: | 3855–4115 |
| Example chimeric hairpin ribozymes: | 4116–4119 |

TABLE 18

Hammerhead Ribozyme Recognition Sites for VEGF

| UCL. POS. | SEQUENCE (5' to 3') | I.D. No. |
|---|---|---|
| 118 | TGCTGCTCtACCTCCACCATG | 4514 |
| 206 | TCATGGATGtCTATCAGCGC | 4515 |
| 254 | GGACATCTtCCAGGAGTAC | 4516 |
| 287 | GTACATCTtCAAGCCATCC | 4517 |
| 386 | CATGCAGATtATGCGGATC | 4518 |
| 402 | ATCAAACCtCACCAAGGCC | 4529 |
| 434 | GATGAGCTtCCTACAGCAC | 4520 |
| 451 | AGAAAAAAAAtCAGTTCGAGG | 4521 |
| 541 | GCAAGAAAtCCCGGTATAA | 4522 |
| 663 | GTACAAGAtCCGCAGACGT | 4523 |

Example 2

Construction of Hairpin Ribozymes

Two single-stranded DNA oligonucleotides are chemically synthesized such that, when combined and converted into double-stranded DNA, they contain the entire hairpin ribozyme, including nucleotides complementary to the target site. In addition, restriction enzyme recognition sites may be placed on either end to facilitate subsequent cloning. More specifically, the oligonucleotides are hybridized together and converted to double-stranded DNA using either Klenow DNA polymerase or Taq DNA polymerase. The resulting DNA is cleaved with restriction enzymes BamHI and AcuI, purified and cloned into vectors for in vitro transcription (pGEM, ProMega, Madison, Wis.) or for retrovirus production and mammalian expression (pLNL/MJT backbone). Representative hairpin ribozymes are set forth below (note that the underlined sequences indicate the sites wherein the ribozyme binds the target sequence):

cde-2 530 (Sequence I.D. No. 4378)
5'
AACGAGCTAGAACCAGACCAGAGAAACACACGTTGTGGTATATTACCTGGTA 3'

Cyclin B1 281 (Sequence I.D. No. 4379)
5'
CTGGCTCAAGAACTGGACCAGAGAAACACACGTTGTGGTATATTACCTGGTA 3'

PCNA 158 (Sequence I.D. No. 4381)
5'
AGCCCTCAAGAAGCAGACCAGAGAAACACACGTTGTGGTATATTACCTGGTA 3'

Defective ribozymes for use as controls may be constructed as described above, with the exception that the sequence AAA is changed to a UGC as shown in FIG. 1.

Example 3

Construction of Hammerhead Ribozymes

Chimeric hammerhead ribozymes (i.e., RNA/DNA hybrids) are designed to have an appropriate NUH sequence for ribozyme cleavage. Ribozymes are chemically synthesized with the general structure shown in FIG. 1. The binding arms bases and stem loop comprise DNA, and the catalytic domain comprises RNA and/or 2'O methyl RNA bases. Specific examples of synthetic human hammerhead ribozymes targeting PCNA are shown below (DNA bases shown in upper case, RNA bases lower case, 2'O methyl RNA as lower case italics, and propanediol shown as pr pr pr pr):

Sequence ID No. 4382: PN30003   PCNI-HH   Length: 40
5' GAGCCCTG cugaugag CAATTTTTTG cgaaa ACCAGGCGC 3'
Sequence ID No. 4383: PN30004   OptPCNI-ome HH   Length: 38
5' AGCCC ug caga u g agg CCGTAAGG cc ga u a cc AGGCGC 3'
Sequence ID No. 4384: PN30005   StabPCNI-ome HH   Length: 38
5' AGCCC ugcu ga u g agg CCGTAAGG cc ga u a cc AGGCGC 3'
Sequence ID No. 4385: PN30006   PCNI-ome HH p4   Length: 28
5' AGCCC ug cuga u g ag pr pr pr pr c ga u a cc AGGCGG 3'

Alteration of the base composition at the stem loop and catalytic domain increases the catalytic activity of the chimeric ribozyme as assayed by in vitro cleavage (EXAMPLE 5). The substitution of 2'O methyl bases for RNA bases enhances the stability of the chimeric ribozymes. The assay consists of incubating 10 μg of ribozyme with 100 μl of cell lysate at 37° C. for times ranging from 30 seconds to 240 minutes, then separating the intact ribozyme from degradation products on a 15% PAGE, staining with SYBRgreen (Molecular Probes, Eugene, OR), and quantifying by phosphorimager analysis (Molecular Dynamics).

Figure 2:
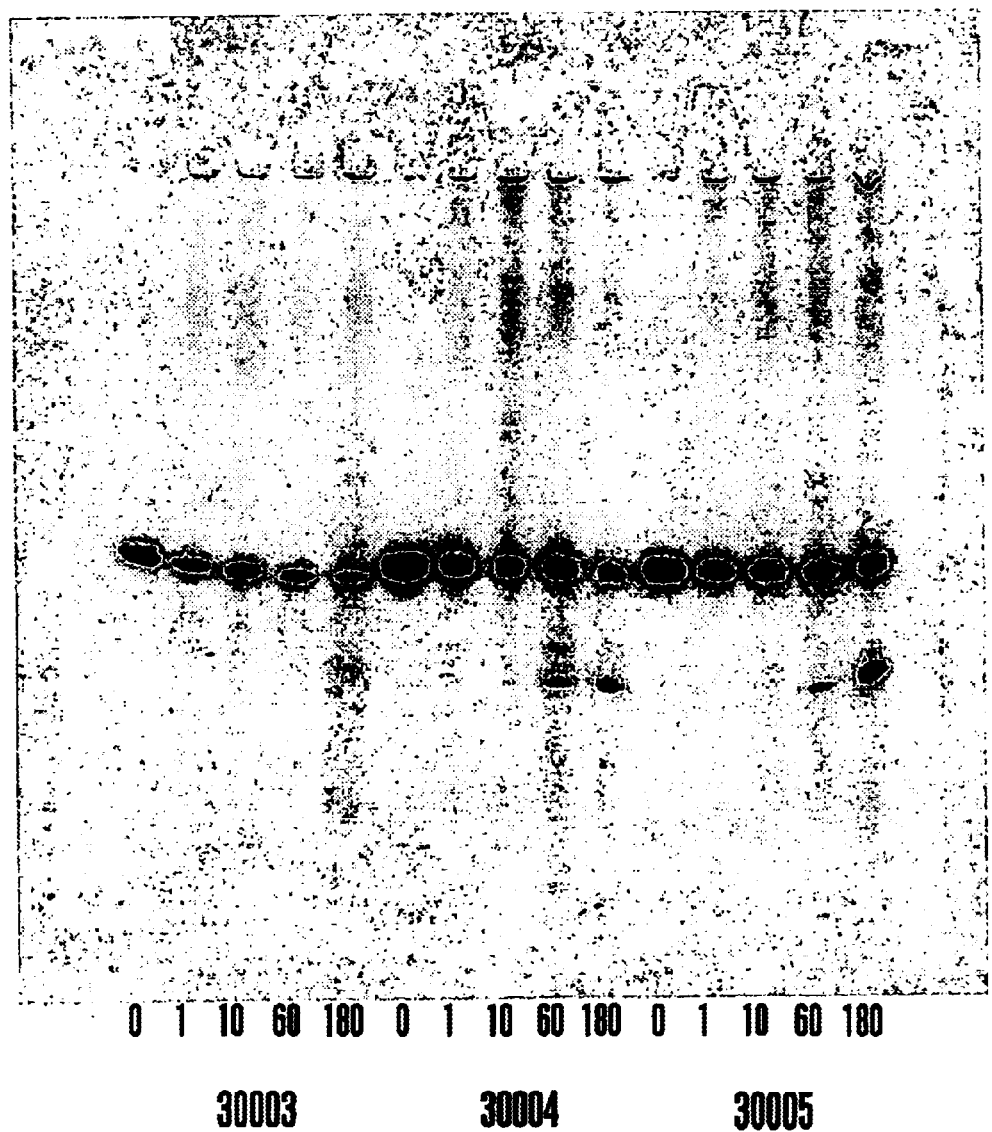
FIG. 2 is a photograph of a gel which shows the stability of chimeric ribozymes PN30003, 30004, and 30005 in human vascular smooth muscle cell lysate.
Figure 3:
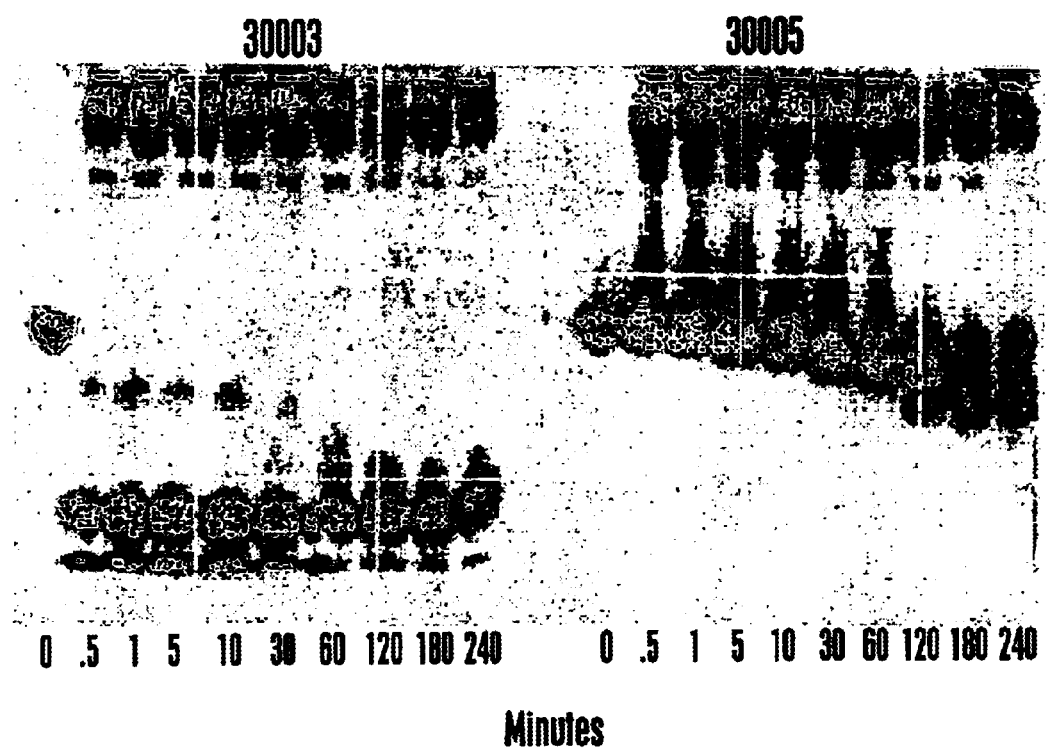
FIG. 3 is a photograph of a gel which shows the stability of chimeric ribozymes PN30003 and 30005 in serum.
Figure 4:
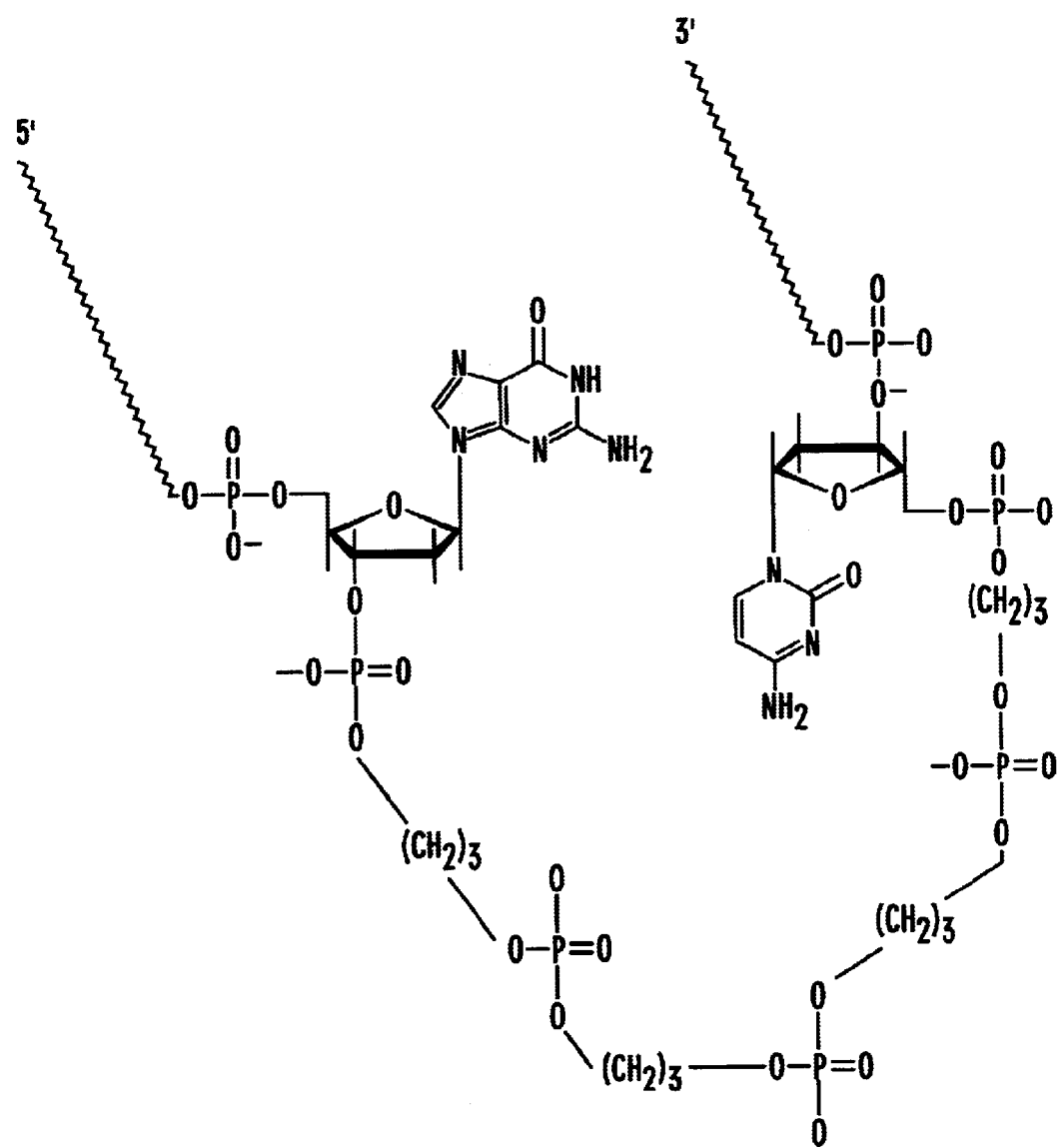
FIG. 4 is a schematic illustration of a propanediol linker.

By making specific base modifications to the structure of the ribozymes, the half-life in cell lysate was increased sequentially from approximately 2.5 hours for PN30003, to 3.5 hours for PN30004, and to greater than 10 hours for PN30005 (FIG. 2). In serum, the half-life of PN30003 is less than 30 seconds. Specific base modifications to ribozyme PN30005 increased the half-life in serum to greater than 4 hours (FIG. 3). The internal stem loop structure can be substituted with a propanediol linkage to shorten the molecule, facilitating delivery, and enhancing catalytic activity (FIG. 4).

A scrambled sequence polynucleotide including the same composition of ribonucleotides and deoxyribonucleotides is also synthesized for each ribozyme to serve as a control with no catalytic activity. Lipofectin may be utilized to enhance the uptake of ribozyme into the cells.

Example 4

Construction of Ribozyme Mammalian Expression Vectors

Figure 5:
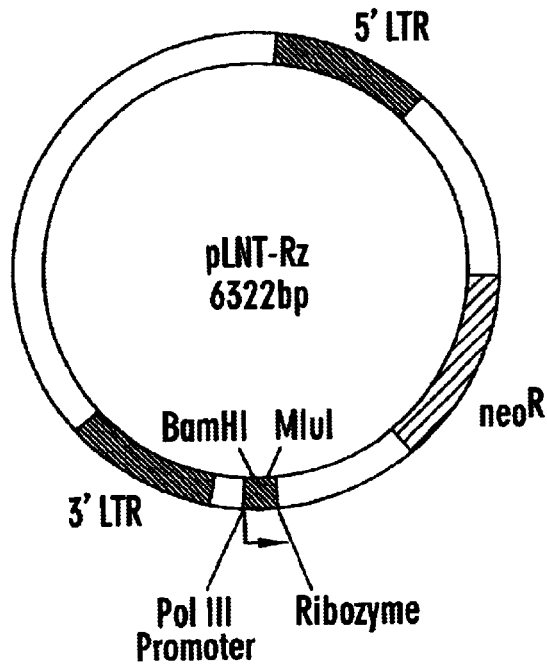
FIG. 5 is a schematic illustration of vector pLNT-Rz.
Figure 6:
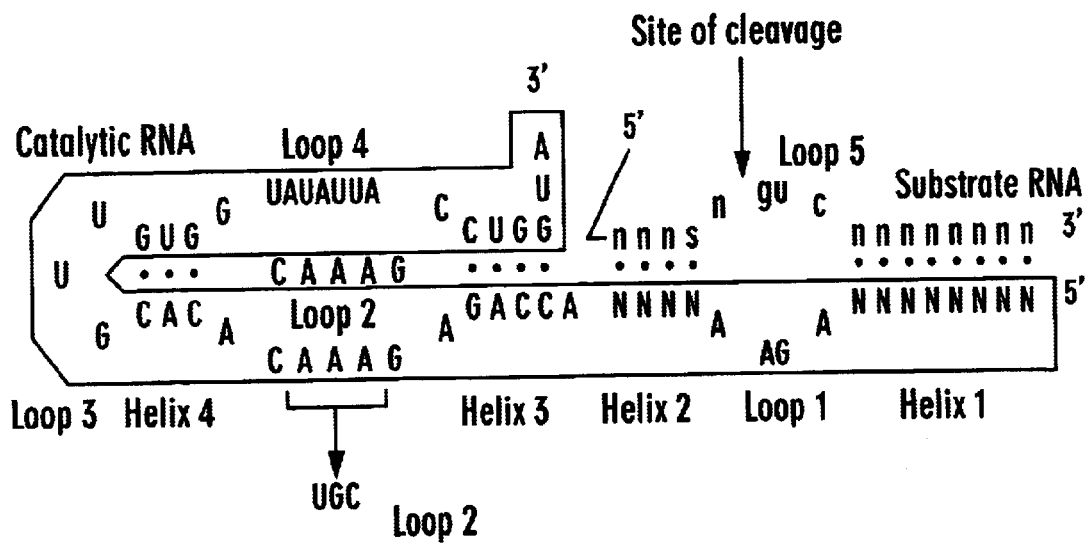
FIG. 6 is a schematic illustration of a representative hairpin ribozyme (SEQ ID NOs: 4387 and 4388).

Plasmid pMJT (Yu et al., *Proc. Nat'l Acad Sci. USA* 90:6340–6344, 1993), which contains the anti-U5 HIV ribozyme driven by the tRNA$^{Val}$ RNA pol III promoter, is digested with BamHI and MluI, and the vector purified from the ribozyme fragment. The hairpin ribozymes, as described above, are excised from the pGem vector with BamHI and AdluI, purified, and ligated into the empty pMJT vector. The resulting vector is designated pLNT-Rz (see FIG. 5, and contains the Moloney LTR driving the neomycin resistance gene and the tRNA$^{Val}$ RNA pol III promoter driving expression of the ribozyme.

Example 5

In Vitro Cleavage Assays

Hairpin or hammerhead ribozymes are tested for cleavage activity in an in vitro assay. Ribozyme and substrate synthesis is achieved by a new method of plasmid-independent in vitro transcription (Welch et al 1997). Briefly, oligonucleotides are synthesized (Retrogen, San Diego, Calif.) with the T7 RNA polymerase promoter sequence contiguous with the ribozyme or substrate sequences, to allow for in vitro transcription of annealed oligonucleotides without the need for plasmid cloning. In vitro cleavage is tested in two hour time course reactions in 40 mM Tris pH 7.5, 10 mM MgCl$_2$, 2 mM spermidine, at 37° C. (Welch et al 1997). Reaction products are analyzed by polyacrylamide gel electrophoresis (PAGE) and quantified by phosphorimager analysis (Molecular Dynamics). The Michaelis constant ($K_m^{app}$) and $k_2$ are determined for each ribozyme by performing single turnover kinetic experiments with ribozyme concentrations of 2–4 nM and substrate concentrations ranging from 2–200 nM, with analysis as above. The $K_m^{app}$ and $k_2$ for the ribozymes is estimated for a Hanes plot with R2>0.90. Catalytic efficiency is calculated as $k_2/K_m^{app}$. In vitro cleavage data for several representative ribozymes targeting specific sites in the CDK4, CDK2, CDC2, cyclin B1, and MMP-1 genes is shown in Table 19.

TABLE 19

Summary of kinetics data for additional hairpin (HP) and hammerhead (HH) ribozyme candidates

|  | HH $k_2/K_m{}^{app}$ | HP $k_2/K_m{}^{app}$ |
| --- | --- | --- |
| CDK4 |  |  |
| cdk4-4 8.9 | 8.33 |  |
| cdk4-4.8g6 |  | 7.3 |
| cdk4-1 7.9 | 6.61 |  |
| CDC2 |  |  |
| cdc2-6/7.8 g7h | 14.4 pig, 31.9 human |  |
| cdc2-6.8g7h |  | 6.25 |
| CDK2 |  |  |
| CDK2-4/7.9 | 27.37 |  |
| CDK2-4.7 |  | 10.76 |
| CYCBI |  |  |
| CycB 8.8 | 9.7 |  |
| MMP-1 |  |  |
| ColR3-9.8 | 0.46 pig, 0.24 human |  |
| ColR9-7.9 | 4615.00 |  |
| ColR1086-9.8 | 52.5 |  |

Example 6

In Vivo Use of Ribozymes

A. Experimental Protocols

All animals are treated according to the guidelines of the Public Health Service Policy on Humane Care and Use of Laboratory Animals.

1. Porcine scar model

Domestic pigs of approximately 35 kg are acclimatized for 14 days to the laboratory environment. Cutaneous lesions are created surgically in five places on the flanks of each pig. Each lesion is 3 cm long×5 mm deep, with a 2 mm slice removed from each lesion site. The wound edges may be sealed by electrocautery. Alternatively, lesions can be created utilizing a 6 mm punch biopsy.

The wound is treated daily by dermal application to each lesion of the desired test substance (with at least 2 untreated control sites per pig). Sites may be bandaged at the direction of the attending veterinarian. All sites are treated identically. Pigs wear protective 'jackets' to prevent mechanical irritation of the lesion sites.

The healing process is scored subjectively on a daily basis (1=fresh lesion, 5—fully healed), and the study terminated when control (untreated) sites score as fully healed.

2. Rabbit Disease Model

Dutch belted rabbits of approximately 2 kg are acclimatized for about 14 days in the laboratory environment. 0.06 Units of dispase is injected intravitreally in order to induce disease. Proliferative vitreoretinopathy (PVR) is then scored on days 1, 7, 14, 28 and 48 (I=0.5=retinal detachment). Typical digital pictures of the process are taken by fundoscopy.

The rabbits are treated on day 21 by injection of either ribozyme or control. The study is terminated when the control (vehicle) sites score as fully detached. Treatment group may be continued if detachment not evident.

B. In vivo results

Figure 7:
FIG. 7 is a photograph of treated and control skin from a porcine model of scar formation.
Figure 7:

An example of the use of the PCNA targeted ribozymes in the porcine scar model is shown in FIG. 7. Panel A shows the effect of vehicle control on two 6 mm punch biopsies after 14 days. Panel B shows the effect of ribozyme treatment on two 6 mm punch biopsies after 14 days. The wound is healed in the treated sample and the extent of scarring is diminished in this example.

Figure 8A:
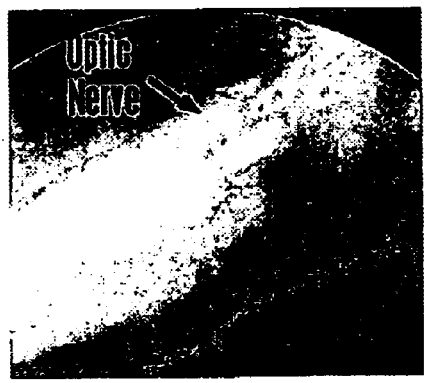
FIG. 8 is a photograph of control eyes and eyes treated with chimeric PCNA targeted ribozyme from a rabbit dispase model of proliferative vitreoretinopathy.
Figure 8B:
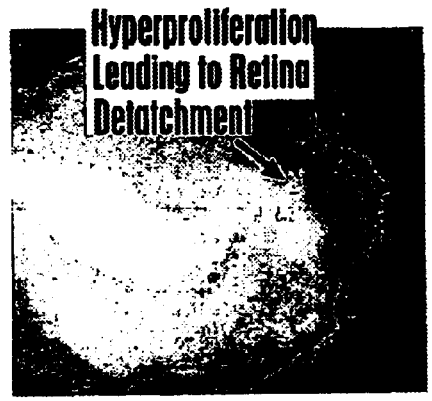
Figure 8C:
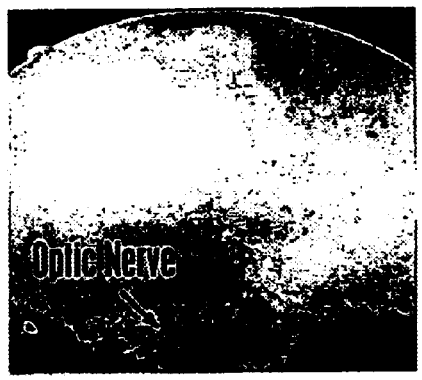

An example of the use of the PCNA targeted ribozymes formulated in DOTAP:cholesterol in the rabbit dispase model is shown in FIGS. 8A–8C. Panel A shows the normal eye. Panel B shows the effect of dispase followed by treatment with vehicle after 31 days. Panel C shows the effect of dispase followed by treatment with ribozyme after 31 days. The retina is complete detached in the vehicle treated eye. The extent of proliferative vitreoretinopathy is diminished and no retinal detachment is evident in the ribozyme treated eye.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

Example 7

In Vitro Percutaneous Absorption of [$^{32}$P]-Ribozyme in Human Cadaver Skin

The example was to evaluate the in vitro percutaneous absorption of eight test formulations of $^{32}$P-labeled ribozyme (PN30006) in tape-stripped and intact human cadaver skin. Cumulative transdermal absorption of radiolabeled drug was measured at 1 and 24 hours. Tissue compartment (stratum corneum, epidermis, dermis) recovery was measured at 24 hours.

Experimental Design:

| Group # (n = 6) | Skin | Formulation Lot # | Ribozyme (% w/w) | Reservoir Samples (Hrs) | Tissue Recovery (Hrs) |
| --- | --- | --- | --- | --- | --- |
| 1 | stripped | 360-34A | 0.5% | 1.24 | 24 |
| 2 | stripped | 360-34B | 0.5% | 1.24 | 24 |
| 3 | stripped | 360-34C | 0.5% | 1.24 | 24 |
| 4 | stripped | 360-34D | 0.5% | 1.24 | 24 |
| 5 | stripped | 360-35E | 0.5% | 1.24 | 24 |
| 6 | stripped | 360-35F | 0.5% | 1.24 | 24 |
| 7 | stripped | 360-35G | 0.5% | 1.24 | 24 |
| 8 | stripped | 360-35H | 0.5% | 1.24 | 24 |
| 9 | Intact | 360-35G | 0.5% | 1.24 | 24 |

Materials

Ribozyme Formulations

| | |
| --- | --- |
| 360-34A | 5 mg/ml ribozyme in 10 mM DTT. 1.5% HEC |
| 360-34B | 5 mg/ml ribozyme in 0.1% SDS. 1.5% HEC |
| 360-34C | 5 mg/ml ribozyme in 5% DMSO. 1.5% HEC |
| 360-34D | 5 mg/ml ribozyme in 15% PG. 1.5% HEC |
| 360-35E | 5 mg/ml ribozyme in 10 mM DTT. 0.1% SDS. 1.5% HEC |
| 360-35F | 5 mg/ml ribozyme in 5% DMSO. 15% PG. 1.5% HEC |
| 360-35G | 5 mg/ml ribozyme in 10 mM DTT. 0.1% SDS. 5% DMSO. 1.5% HEC |
| 360-35H | 5 mg/ml ribozyme in 10 mM DTT. 5% DMSO. 15% PG. 1.5% HEC |

Key to abbreviations:
  DTT Dithiotheitol (reducing agent)
  HEC Hydroxyethylcellulose (gelling agent)
  SDS Sodium docedyl sulfate (penetration enhancer)
  DMSO Dimethyl sulfoxide (penetration enhancer)
  PG Propylene glycol (penetration enhancer)
Human Skin:
  Human cadaver skin was obtained from a single donor. The skin was dermatomed to approximately 200 micron thickness. Skin was excluded if it was damaged, had irregularities (scar tissue, holes, birthmarks, etc.) or was from donors with infectious disease. Skin samples were frozen until use. Skin specimens were thawed overnight in the refrigerator in plastic sealed bags prior to the experiment.
Spiking Test Formulations:
  Test formulations were spiked with [$^{32}$P]-ribozyme prior to the experiment. 15 il of the radiolabeled solution was added to 1.0 gram (ml) of the formulation and spatulated.
  To assay the final specific activity of the spiked test formulation, approximately 10–30 mg of the formulation was weighed (n=3). 100 µl samples were placed in 10 ml of Ecoscint$^R$ scintillation fluor (National Diagnostics #LS275) and counted in a Beckman Model LS 3801 liquid scintillation counter with a pre-calibrated quench curve for $^{32}$P. Thirty (30) mg of spiked formulation was applied to each chamber. The total DPM of the applied dose was calculated by determining the total DPM applied in the 30 mg dose and subtracting the DPM of the application tips.
Equipment:
  A total of 54 Franz static diffusion glass diffusion chambers (Crown Glass Cat #FDC-100) with a magnetic stirrer mounted on a 9-position Franz diffusion cell drive console with acrylic blocks, magnetic stirrers, and stainless steel manifolds (Crown #FDCD-9-LV) was used for the study. The reservoir volume (6–11 ml) of each cell was pre-calibrated.
Equipment Set-up:
  The diffusion cells were filled with 4% bovine serum album (BSA, Fraction V) (Sigma Cat. #A2153) in isotonic buffered (pH 7.04) saline (PBS Fisher Cat #C5551-20 Celline-II isotonic saline solution) with care to avoid bubbles at the skin interface. The diffusion cells were equilibrated for 1–2 hours to a temperature of 37° C. by a circulating water pump (Haake) prior to applying skin specimens.
Application of Drug to Skin:
  The intact or prior tape-stripped dermatomed human cadaver skin was placed on the chamber and sealed with an O-ring. The skin surface area exposed to the test formulations was 1.77 cm$^2$. The skin was equilibrated for 30 minutes at 37° C. on the diffusion cell prior to applying test formulation. A total of 30 mg of the spiked formulation was applied to the skin surface using a Gilson Microman$^R$ positive displacement pipette and gently rubbed into the skin using the pipette tip. The dispensing tips were retained and counted. The mean DPM retained by the dispensing tips was calculated and subtracted from the theoretical DPM to determine the mean total DPM applied to each chamber.
Sample Collection:
  Reservoir:
  At 1 and 24 hours a 1.0 ml sample was removed from the reservoir using a calibrated Gilson P1000 Pipetteman$^R$ micropipette, and the volume replaced with 1.0 ml BSA-saline solution. The samples were placed in a scintillation vial containing Ecoscint$^R$ scintillation fluor (National Diagnostics #LS-275) and equilibrated overnight in the dark before counting.

Figure 9:
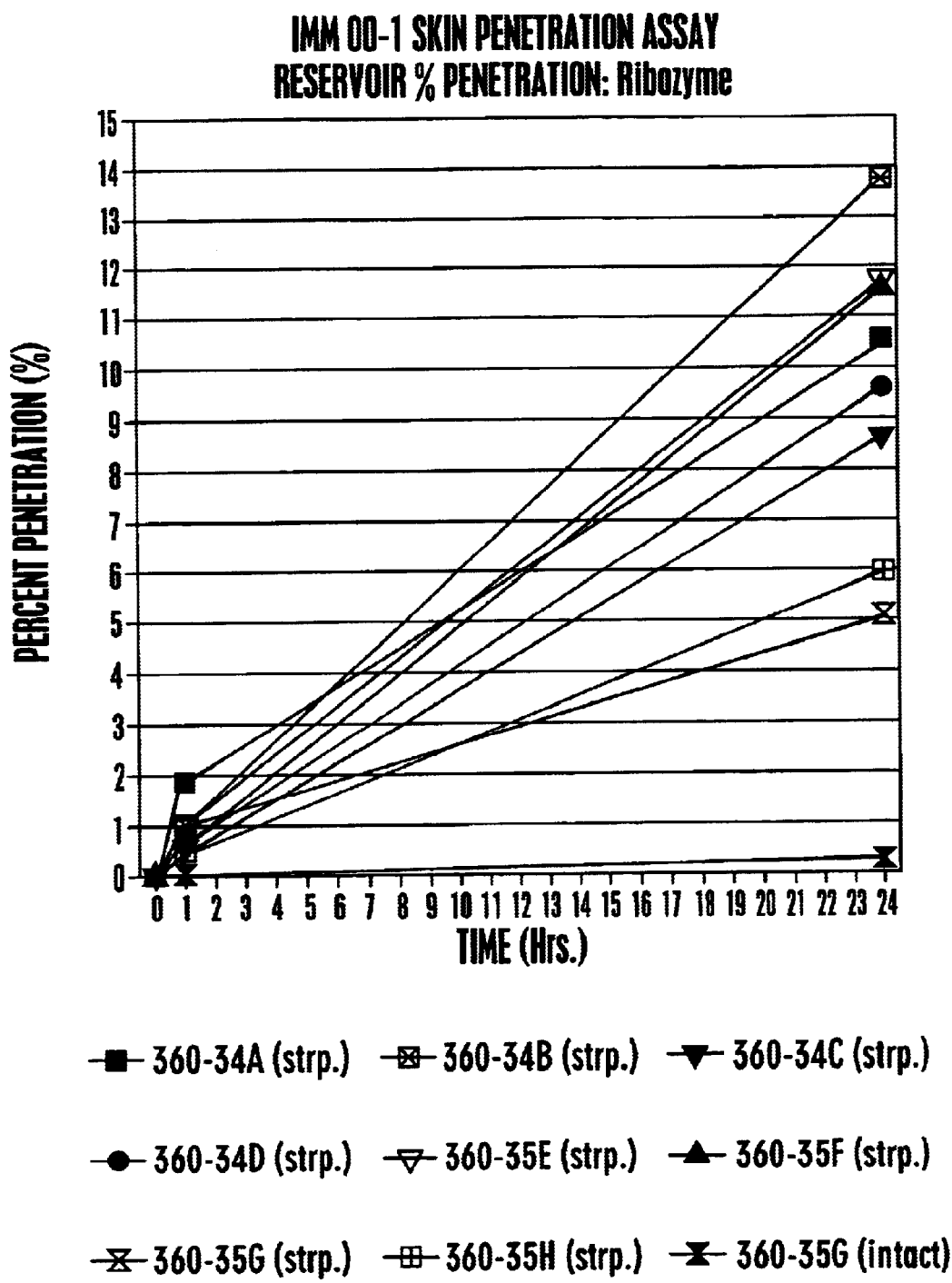
FIG. 9 is a chart of the cumulative transdermal absorption of $^{32}$P-ribozyme presented as the percent of the applied dose recovered in the reservoir of diffusion chambers.
Figure 10:
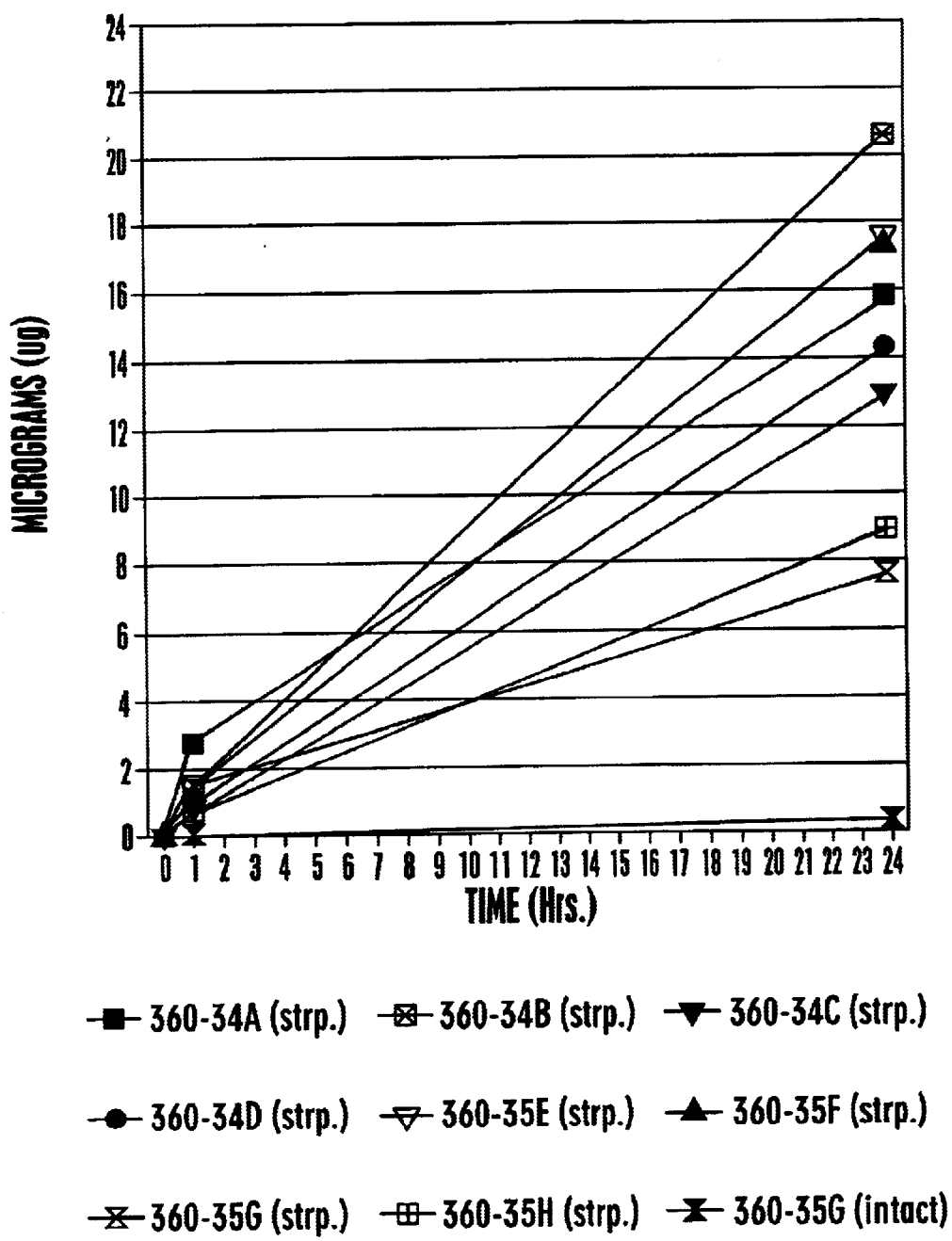
FIG. 10 is a chart of the cumulative transdermal absorption of $^{32}$P-ribozyme presented as total micrograms recovered in the reservoir of diffusion chambers.
Figure 11:
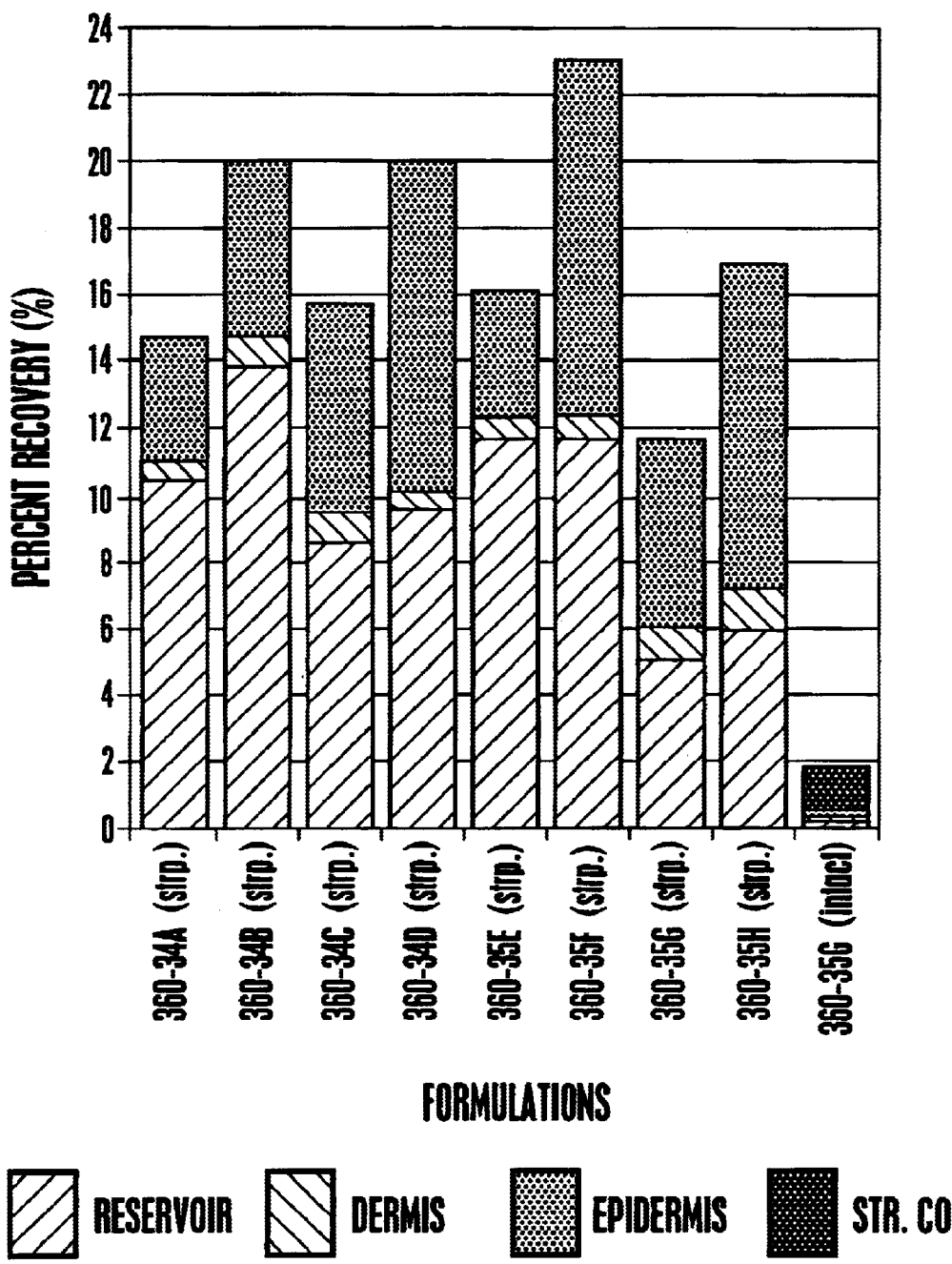
FIG. 11 is a chart of the localization of $^{32}$P-ribozyme in various skin compartments presented as percent of the applied dose recovered in each compartment.
Figure 12:
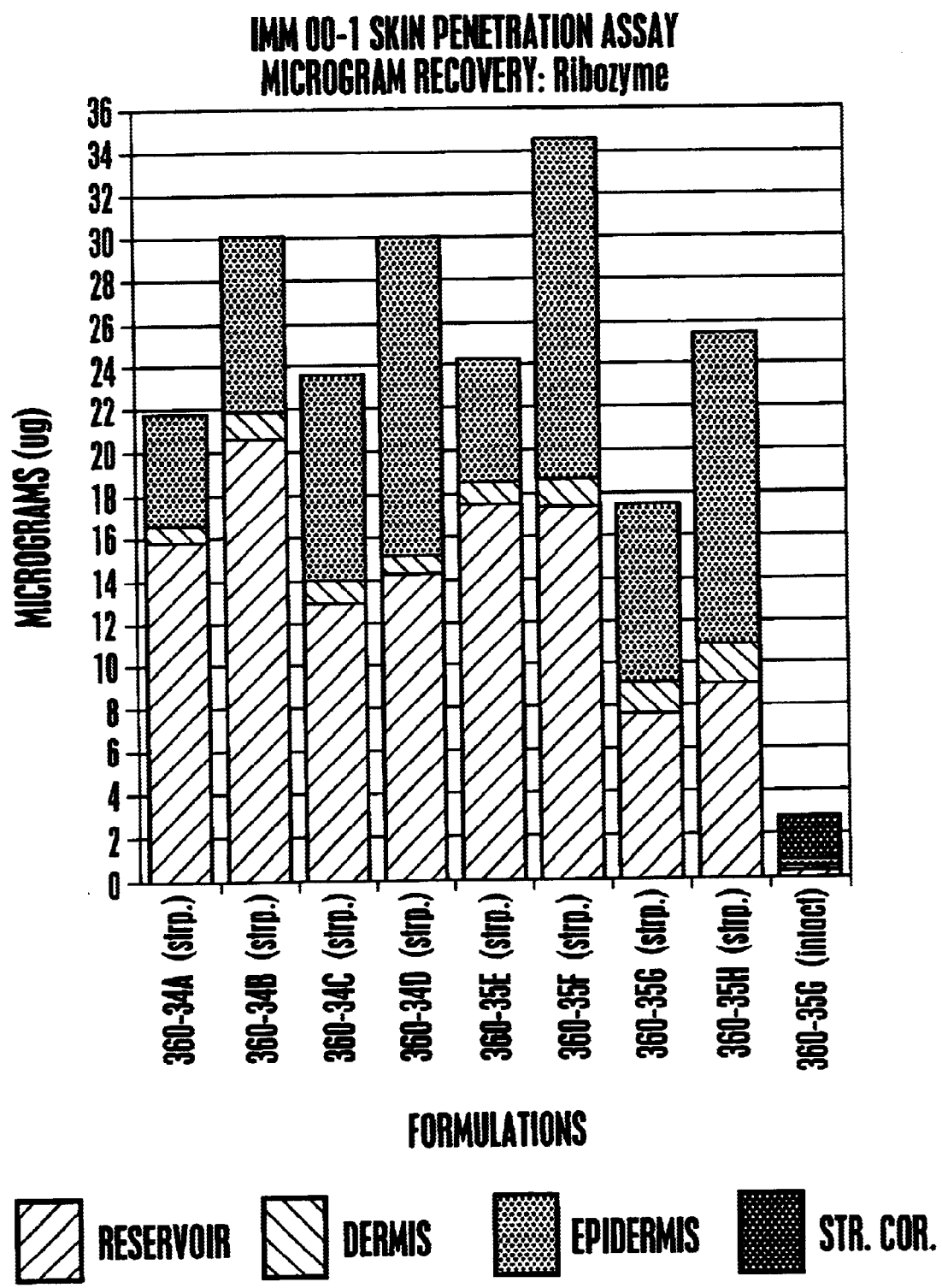
FIG. 12 is a chart of the localization of $^{32}$P-ribozyme in various skin compartments presented as total micrograms in each compartment.

Washes and Gauze Wipes:
  At 24 hours the skin surface was washed three times with 1.0 ml 2% Oleth-20 (Croda, Inc. #9004-98-2) in water, followed by 2 washes with 1.0 ml of 5% Span 80 in isopropanol. The wash solutions were collected for recovery counts. The dispensing tips used for the washing procedure were also counted and included in the "wash" compartment. After washing, the skin surface was wiped with 3 sequential cotton gauze cloths, which were saved for recovery counts in the "Gauze" compartment.
  Tape Stripping (Stratum Corneum):
  The skin specimens were either tape-stripped prior to drug application or following the gauze wiping. The skin was placed dermis side down onto a flat surface. The stratum corneum was removed by tape-stripping the skin with cellophane tape until "glistening" (approximately 22 strips) or until epidermal separation started to occur. The first two strips that remove the excess drug adhering to the outer surface of the stratum corneum were counted separately. These counts were included in total recovery (SC Surface) but excluded from stratum corneum compartment recovery. Four groups each consisting of five consecutive tape strips were placed in a scintillation vial containing Scintilene$^R$ (Fisher #SX2-4).
  Epidermis and Dermis:
  After tape-stripping the intact skin or after removing the tape-stripped skin from the chamber, the dermis and epidermis were separated by microwave technique (2–5 sec.). The separated epidermis was placed in a vial containing 1 ml of Soluene 350 (Packard, Inc #6003038), and dermis in vial containing 2 ml Soluene 350. The tissues were then digested in a 60° C. oven for 4 hours. Hionic-Fluor (Packard, Inc #6013319) was added to the digested tissues, counted in a Beckman LSC and corrected for quenching.
Recovery:
  The percent of $^{32}$P-ribozyme recovered in the reservoir, washes, gauze wipes, and skin compartments (stratum corneum, epidermis, dermis) was determined by calculating the percent of the total applied DPM recovered in the respective compartments.
  The total micrograms of drug recovered in each compartment was obtained by multiplying the % recovery by the total amount (micrograms) of drug applied to each chamber.
Data Entry/Calculations:
  The DPM data from the LSC tapes, measurements for cell volume, and quantity of drug applied were entered into a standardized Quattro Pro spreadsheet. The data were calculated after discarding outlier values for each compartment. A value was considered to be an "outlier" if the questionable value differed from the re-calculated average by more than four times the average deviation of the remaining values (Skoog & West, Analytical Chemistry).
Results
  The total DPM applied to each cell ranged from 12–15× 10$^6$. The cumulative transdermal absorption of $^{32}$P-ribozyme is presented as the percent of the applied dose recovered in the reservoir at each time point (FIG. 9). The transdermal absorption of $^{32}$P-ribozyme is also presented as total micrograms recovered in the reservoir (FIG. 10). The total 24 hr flux in the tape-stripped skin ranged from 5–12% compared to 0.2% in the intact skin.
  The localization of $^{32}$P-ribozyme in the various skin compartments is presented as both percent of the applied dose (DPM) recovered in each compartment (FIG. 11) and total micrograms in each compartment (FIG. 12). The recovery of the formulations in the dermal tissues was similar in the tape-stripped skin, ranging from 0.5–1.0% of the applied dose compared to 0.1% in the intact skin. The recovery of all formulations was high in the epidermis in the tape-stripped skin ranging from 3–10% compared to 0.2% in the intact skin.

Tables 20 and 21 rank the absorption (%, ig) of the test formulations for the sum of the recoveries in the reservoir, epidermis and dermis.

TABLE 20

Overall effectiveness (percent)

| Relative Effectiveness | Skin | Formulation Lot # | Ribozyme (% w/w) | Description | SUM (Reservior, Epi. Dermis) % |
|---|---|---|---|---|---|
| 1 | stripped | 360-34A | 0.5 | Cream | 23.1 |
| 2 | stripped | 360-34B | 0.5 | Cream | 20.1 |
| 3 | stripped | 360-34C | 0.5 | Cream | 20.0 |
| 4 | stripped | 360-34D | 0.5 | Cream | 17.0 |
| 5 | stripped | 360-35E | 0.5 | Cream | 16.2 |
| 6 | stripped | 360-35F | 0.5 | Cream | 15.7 |
| 7 | stripped | 360-35G | 0.5 | Cream | 14.6 |
| 8 | stripped | 360-35H | 0.5 | Cream | 11.7 |
| 9 | Intact | 360-35G | 0.5 | Cream | 0.5 |

TABLE 21

Overall effectiveness (micrograms)

| Relative Effectiveness | Skin | Formulation Lot # | Ribozyme (% w/w) | Description | SUM (Reservior, Epi. Dermis) % |
|---|---|---|---|---|---|
| 1 | stripped | 360-34A | 0.5 | Cream | 34.7 |
| 2 | stripped | 360-34B | 0.5 | Cream | 30.1 |
| 3 | stripped | 360-34C | 0.5 | Cream | 29.9 |
| 4 | stripped | 360-34D | 0.5 | Cream | 25.5 |
| 5 | stripped | 360-35E | 0.5 | Cream | 24.3 |
| 6 | stripped | 360-35F | 0.5 | Cream | 23.6 |
| 7 | stripped | 360-35G | 0.5 | Cream | 21.8 |
| 8 | stripped | 360-35H | 0.5 | Cream | 17.5 |
| 9 | Intact | 360-35G | 0.5 | Cream | 0.8 |

Example 8

Inhibition of Experimental PVR by Ribozymes Targeting Rabbit PCNA

A. Experimental PVR treated with Ribozyme:Lipid Complex

Experimental design

The rabbit model involves the injection of dispase into the vitreal space without the need to introduce retinal tears. Prior models have relied on exogenous cells such as fibroblasts to induce disease. In the dispase model, no assumptions are made as to the type of endogenous cells involved in the formation of disease. The severity of PVR correlated with the dose of dispase injected. The optimal dose of dispase has been determined to minimize interfering complications such as cataract and hemorrhage. This model uses intravitreal rather than subretinal injection. The timing and complexity of the cellular response correspond to the human disease. These advantages make this model particularly attractive. The single disadvantage of relatively long timeframe is easily overcome by extending the period of observation. This model was used to test the efficacy of the chimeric PCNA targeted ribozyme.

A selected lot of dispase was tested in the rabbit eye to titrate the dose and time frame for disease development and aliquots frozen for all remaining experiments (Frenzel E M, Neely K A, Walsh A W, Cameron J D, Gregerson D S, 1998. A new model of proliferative vitreoretinopathy, IOVS 39:2157–2164). Twelve 1–2 Kg Dutch Belted rabbits received a single intravitreal injection of 0.06, 0.07, or 0.08 U dispase (Boehringer Mannheim, Indianapolis, Ind.) on day 0 (four rabbits each dose). Rabbits were anesthetized with ketamine/xylazine, their eyes dilated with 2.5% phenylephrine and 1% tropicamide, and a local anesthetic, proparacain HCl applied. 0.1 cc of dispase was injected into the right eye of each rabbit with a 30 gauge needle, delivering the dispase into the vitreous cavity directly in front of the retina without traumatizating the retina, under direct visualization with a dissecting microscope equipped with floating Charles lens. Left eyes serve as controls. Rabbits were followed for progression of disease by fundoscopy at days 1, 7, 14, 21, 28, and 48. A generous timeframe was allocated to maximize the probability of disease development in the dispase treated groups. Fundoscopic evaluation was by two independent, trained observers for this and the following experiments. In this experiment, a dose of 0.07 U dispase resulted in uniform PVR development by 21 days.

Following the same protocol, a second experiment was performed with eight rabbits given 0.07 U dispase in the right eye on day 0. At 7–14 days post-injection, all eyes had vitreous and pre-retinal hemorrhage. At 21 days 7 of 8 rabbits had early PVR characterized by fibroglial proliferation. Before a retinal detachment was noted in any eyes, the control group of rabbits (n=4) was treated with an intravitreal injection of 0.1 cc DOTAP:cholesterol vehicle. The experimental group (n=4) was given an intravitreal injection of 0.1 cc chimeric PCNA targeted ribozyme (PN30006).

Fundoscopic analysis

Fundoscopic evaluation of chimeric PCNA targeted ribozyme versus control treated rabbit eyes is the same as shown in FIGS. 8A–8C. By day 35, all rabbits in the control group developed significant retinal detachment. Three of four in the chimeric PCNA targeted ribozyme treated group did not develop a retinal detachment, while one developed a small local detachment, which did not progress over the 60 day follow-up period. These data suggest that inhibiting proliferation of cells causative of PVR with chimeric ribozyme to PCNA may have a therapeutic or preventative role.

Figure 13:
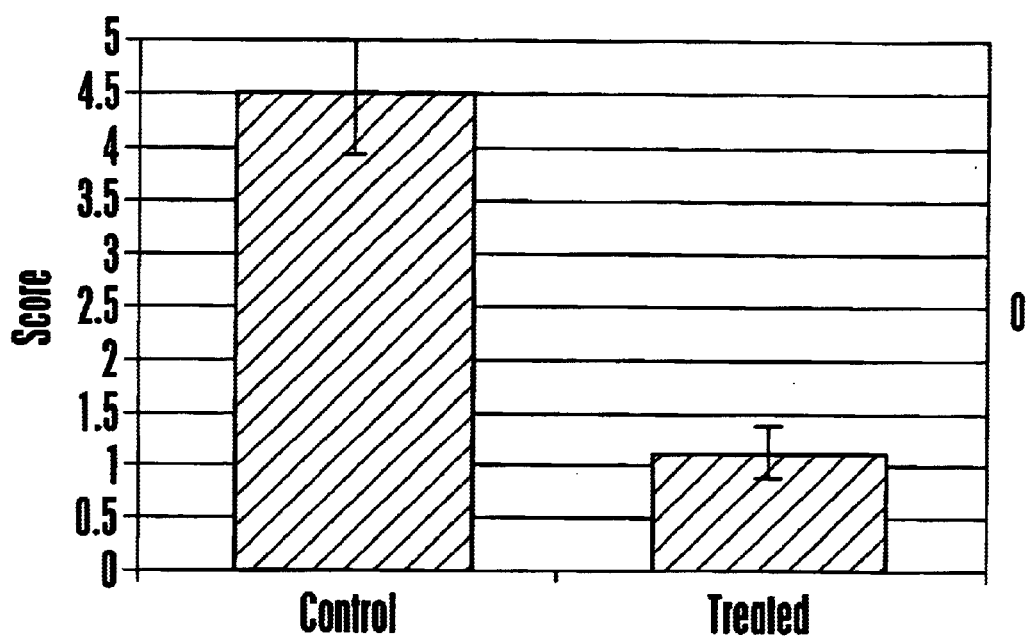
FIG. 13 is a chart of histopathologic scoring of chimeric PCNA targeted ribozyme versus control treated rabbit eyes. Scoring is based on a modified Fastenberg scale (Table 22) and performed blindly by two trained observers. P is less than 0.0008 by T test.

All eyes were scored by two independent trained observers on a scale of 1–6 as per Table 22 (Fastenberg et al. 1982. A comparison of different cellular inocula in an experimental model of massive periretinal proliferation. Am J Ophthalmol. 93:559–56; Sakamoto et al. 1995. Inhibition of experimental proliferative vitreoretinopathy by retroviral vector-mediated transfer of suicide gene. Ophthalmology 102:1417–1424). The scale is based on inflammation, hemorrhage, distortion, intravitreal haze and membranes, and formation of retinal breaks, traction, and detachments. The results (FIG. 13) indicate that the chimeric ribozyme is effective in preventing or retarding the development of PVR.

TABLE 22

Histopathologic scoring of PVR

| Score | Histopathologic Evaluation |
|---|---|
| 0 | Normal eye |
| 1 | Hemorrhage/preretinal gliotic changes |
| 2 | Focal Retration |
| 3 | Extensive PVR with focal traction |

TABLE 22-continued

Histopathologic scoring of PVR

| Score | Histopathologic Evaluation |
|---|---|
| 4 | PVR with focal retinal detachments of medullary ray |
| 5 | Extensive peripapillary retinal detachments |
| 6 | Total retinal detachments |

Histopathologic analysis

Treated and control eyes were enucleated, fixed in 4% paraformaldehyde, embedded in paraffin, and sectioned for histopathologic evaluation. Selected gross specimens were photographed before sectioning. Histologic examination was performed after hematoxylin and eosin staining. Histopathologic analyses correlated with the gross pathological findings and confirmed the clinical diagnoses of PVR and retinal detachment.

The ability of this chimeric ribozyme complex to prevent or lessen the degree of damage due to aberrant proliferation of cells in the eye could be a significant advancement in the treatment of PVR. This type of therapy may be especially well suited for use in patients facing vision loss due to the failure of traditional surgical treatment (McCormack P, Simcock P R, Charteris D, Lavin M J. 1994. Is surgery for proliferative vitreoretinopathy justifiable? Eye 8:75–76).

B. Experimental PVR treated with Ribozyme Alone

Three additional experiments in the PVR model were carried out. Experiment 2 was a repeat of the first experiment described above (i.e., Example 8, Section A) with the addition of a control group with scrambled sequence (random specificity) ribozyme complexed to the lipid. The other two experiments were done using the ribozyme alone at 10 mg/ml without the addition of the DOTAP:cholesterol lipid. These were done due to an observed precipitate that took greater than 2 weeks to clear. The precipitate was not observed when lipid was absent. Experiment 3 repeated the timing of the first two experiments, with ribozyme treatment on day 20. Experiment 4 was performed with treatment on day 7 to represent a prophylactic approach. The overall severity of the PVR has decreased over time even in the control group consistent with loss of activity of the dispase. The results are shown in table 23 where two independent assessments were made by trained observers using a modified Fastenberg et al. (1982) scoring system (i.e., Table 22).

TABLE 23

Scoring of ribozyme and control treated rabbit eyes with Dispase induced PVR.

| Exp # | | Ribozyme | Lipid | N | Treatment Day | Assessment Day | Ave. Score |
|---|---|---|---|---|---|---|---|
| 2 | Treated | PN30004 | + | 4 | 20 | 35 | 3.1 ± 1.3 |
| | Control | Scrambled | | 4 | | | 5.3 ± 1.2 |
| | | Dextrose | | 4 | | | 4.5 ± 1 |
| 3 | Treated | PN30006 | − | 4 | 20 | 49 | 1.8 ± 1.7 |
| | Control | Dextrose | | 3 | | | 3.7 ± 0.6 |
| | | no injection | | 2 | | | 2.5 ± 0.7 |
| 4 | Treated | PN30006 | − | 6 | 7 | 28 | 0.7 ± 0.8 |
| | Control | Dextrose | | 6 | | | 2.2 ± 0.4 |

The results show a consistent decrease in severity of PVR following treatment with active chimeric PCNA targeted ribozyme compared to untreated or scrambled ribozyme controls.

Example 9

Effects of PCNA Targeted Ribozyme on Scar Formation in the Pig

Figure 14A:
FIG. 14A and FIG. 14B are two photographs of a surgical wound model in pig skin.
Figure 14B:
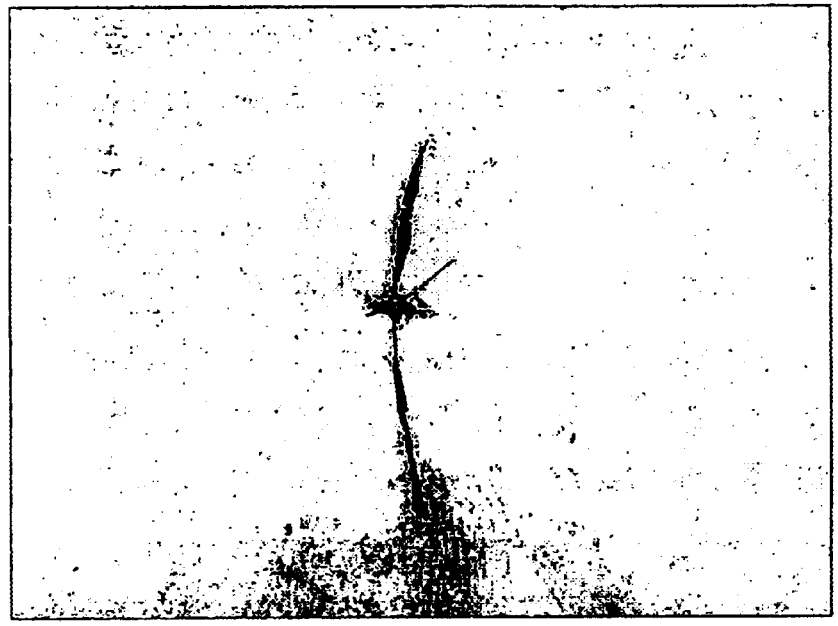

A chimeric PCNA targeted ribozyme (PN30006) has been tested in a pig model of scarring due to surgical incision. Briefly, two female commercial pigs underwent surgical creation of wounds followed by administration of the test or vehicle article into selected wounds for three consecutive days. Crescent shaped wound sites (5 on each side), each measuring approximately 3 cm long×5 mm deep×6 mm wide, were made on the back of each animal (FIG. 14A). Each wound was sutured once (FIG. 14B). This type of wound was made to replicate excisional wounding. Wounds were dressed with an Op-site bandage immediately after instillation of the test article on Days 1, 2 and 3. Animals were bandaged and dressed in restraining jackets to prevent mechanical irritation of the surgical sites (as necessary).

Visual observations made in the in-life phase were scored as follows: 1 completely healed/scarred, 2 scab exfoliating, 3 wound scabbing, 4 open wound. Histopathologic evaluation was done at 36 days, and included scoring for: epithelialization, inflammation, scar tissue, and connective tissue.

There were no treatment related clinical signs following instillation of the test or vehicle articles into selected wound sites for 3 consecutive days. All clinical signs that were observed (red skin, exudate, scabbing) were considered to be part of the normal healing process for surgical wounds of the type created on this study.

All wound sites were prepared for histopathological examination by embedding in paraffin wax, sectioning and staining with hematoxylin and eosin/phloxine. Histopathological examination was conducted on all wound sites from both animals to evaluate the following parameters:

| | |
|---|---|
| a. Re-epithelialization | Present, partial, or absent epithelialization of the surface epithelium. |
| b. Inflammation | Degree of severity, cell type and distribution. |
| c. Scar Tissue Formation | Presence or absence of scar tissue, extent, size, depth and severity of scarring. |
| d. Connective Tissue Formation | Presence or absence of collagen and connective tissue associated with normal healing, the extent, size and depth (as opposed to scar tissue formation). |

Scarring in comparison to healing was differentiated by the amount of connective tissue, the amount of neovascularity, inflammation, and amount of normal subcutaneous collagen present. In the scarred lesions, there was more connective tissue and the plug area was clearly differentiated from the adjacent normal tissue, while in the more healed or drug treated lesions, the plug area was almost contiguous with the adjacent tissue and difficult to differentiate from the adjacent tissue.

Histopathological examination failed to detect any negative long term consequences on epithelialization by drug treatment since complete healing occurred at all wound sites. Additionally, there was no correlation between treatment and inflammation. Histopathological examination of wound sites 36 days after wounding revealed that chimeric PCNA targeted ribozyme treated wounds were more completely healed and less scarred than untreated wounds or wounds treated with the vehicle article.

SEQUENCE LISTING

The patent contains a lengthy "Sequence Listing" section. A copy of the "Sequence Listing" is available in electronic form from the USPTO web site (http://seqdata.uspto.gov/sequence.html?DocID=5876714B9). An electronic copy of the "Sequence Listing" will also be available from the USPTO upon request and payment of the fee set forth in 37 CFR 1.19(b)(3).

We claim:

1. A method of treating a proliferative eye disease, comprising administering locally to a patient a therapeutically effective amount of a ribozyme which cleaves RNA encoding a cyclin PCNA, such that said proliferative eye disease is treated, said RNA comprising SEQ ID NO: 4145, wherein the binding arms of said ribozyme bind to SEQ ID NO:4145.

2. A method of treating a proliferative eye disease, comprising administering locally to a patient an effective amount of a nucleic acid molecule comprising a promoter operably linked to a nucleic acid segment encoding a ribozyme which cleaves RNA encoding a cyclin PCNA, such that said proliferative eye disease is treated, said RNA comprising SEQ ID NO: 4145, wherein the binding arms of said ribozyme bind to SEQ ID NO:4145.

3. The method according to claims 1 or 2 wherein said proliferative eye disease is proliferative diabetic retinopathy.

4. The method according to claims 1 or 2 wherein said proliferative eye disease is proliferative vitreoretinopathy.

5. The method according to claims 1 or 2 wherein said proliferative eye disease is proliferative sickle cell retinopathy.

6. The method according to claims 1 or 2 wherein said proliferative eye disease is retinopathy of prematurity.

7. The method according to claims 1 or 2 wherein said proliferative eye disease is retinal detachment.

8. The method according to claims 1 or 2 wherein said ribozyme is a hammerhead or hairpin ribozyme.

9. The method according to claim 1, wherein said ribozyme is administered intraocularly.

10. The method according to claim 1 wherein said ribozyme is formulated within a solution.

11. The method according to claim 1 wherein said ribozyme is formulated along with a lipid.

12. The method according to claim 11 wherein said lipid is DOTAP:cholesterol.

13. The method according to claim 1 wherein said ribozyme is formulated with ribonuclease inhibitors.

14. The method according to claim 13 wherein said ribonuclease inhibitor is a reducing agent.

15. The method according to claim 14 wherein the reducing agent is dithiothreitol.

16. The method according to claim 13 wherein said ribonuclease inhibitor is a detergent.

17. The method according to claim 16 wherein the detergent is sodium dodecyl sulfate.

18. The method according to claim 13 wherein said ribonuclease inhibitor is vanidyl nucleotides.

19. The method according to claim 13 wherein said ribonuclease inhibitor is aurin tricarboxcylic acid.

20. The method according to claim 13 wherein said ribonuclease inhibitor is hydrogen peroxide.

21. The method according to claim 13 wherein said ribonuclease inhibitor is an RNA decoy.

22. The method according to claim 21 wherein said RNA decoy is a tRNA.

23. The method according to claim 1 wherein said ribozyme comprises ribonucleic acids.

24. The method according to claim 1 wherein said ribozyme comprises deoxyribonucleic acids and ribonucleic acids.

25. The method according to claim 1 wherein said ribozyme comprises nucleic acids having phosphothioate linkages.

26. The method according to claims 1 or 2 wherein said ribozyme comprises a sequence selected from the group consisting of SEQ ID NOS: 4383 and 4385.

27. The method of claim 26, wherein said sequence is SEQ ID NO: 4385.

28. The method according to claim 2 wherein said nucleic acid molecule is administered intraocularly.

* * * * *